US011883291B2

(12) United States Patent
Gifford, III et al.

(10) Patent No.: US 11,883,291 B2
(45) Date of Patent: Jan. 30, 2024

(54) VALVE REPAIR DEVICES WITH COAPTATION STRUCTURES AND MULTIPLE LEAFLET CAPTURE CLIPS

(71) Applicant: Half Moon Medical, Inc., Menlo Park, CA (US)

(72) Inventors: Hanson S. Gifford, III, Woodside, CA (US); Ben F. Brian, Menlo Park, CA (US); Matthew McLean, San Francisco, CA (US); Gaurav Krishnamurthy, Mountain View, CA (US); Neil Zimmerman, Menlo Park, CA (US); James I. Fann, Portola Valley, CA (US); Katherine Miyashiro, Menlo Park, CA (US)

(73) Assignee: Half Moon Medical, Inc., Menlo Park, CA (US)

( * ) Notice: Subject to any disclaimer, the term of this patent is extended or adjusted under 35 U.S.C. 154(b) by 240 days.

(21) Appl. No.: 17/027,681

(22) Filed: Sep. 21, 2020

(65) Prior Publication Data
US 2021/0085462 A1    Mar. 25, 2021

Related U.S. Application Data

(60) Provisional application No. 62/902,694, filed on Sep. 19, 2019.

(51) Int. Cl.
*A61F 2/24*    (2006.01)

(52) U.S. Cl.
CPC ............ *A61F 2/2463* (2013.01); *A61F 2/246* (2013.01); *A61F 2/2445* (2013.01); *A61F 2/2454* (2013.01); *A61F 2220/0008* (2013.01)

(58) Field of Classification Search
CPC ...... A61F 2/2463; A61F 2/2445; A61F 2/246; A61F 2/2454; A61F 2220/0008; A61F 2250/0069
See application file for complete search history.

(56) References Cited

U.S. PATENT DOCUMENTS

| 6,869,444 | B2 | 3/2005 | Gabbay |
| 7,160,322 | B2 * | 1/2007 | Gabbay ................. A61F 2/2454 |
| | | | 623/2.11 |

(Continued)

FOREIGN PATENT DOCUMENTS

| EP | 2819618 A1 | 1/2015 |
| EP | 3167846 A1 | 5/2017 |

(Continued)

OTHER PUBLICATIONS

ISA, PCT Application No. PCTUS2018/061126, International Search Report and Written Opinion dated Jul. 9, 2019, 12 pages.

(Continued)

*Primary Examiner* — Paul B Prebilic
(74) *Attorney, Agent, or Firm* — Perkins Coie LLP

(57) ABSTRACT

Cardiac valve repair devices with coaptation members and multiple clip mechanisms and associated systems and methods are disclosed herein. A cardiac valve repair device configured in accordance with embodiments of the present technology can include, for example, an optional fixation member configured to engage tissue within a left atrium proximate to a native mitral valve, a coaptation member depending from the fixation member, and a plurality of clip mechanisms extending from a downstream portion of the coaptation member. The coaptation member can be positioned between the native leaflets and at least partially fill a space between the native leaflets. A first clip mechanism can engage a first portion of one of the native leaflets, and a second clip mechanism can engage another portion of the same native leaflet or an opposing native leaflet.

44 Claims, 9 Drawing Sheets

(56) References Cited

U.S. PATENT DOCUMENTS

| | | | |
|---|---|---|---|
| 9,011,523 B2* | 4/2015 | Seguin | A61F 2/2427 623/2.11 |
| 9,592,118 B2 | 3/2017 | Khairkhahan et al. | |
| 9,592,121 B1* | 3/2017 | Khairkhahan | A61F 2/2454 |
| 9,610,163 B2* | 4/2017 | Khairkhahan | A61B 17/068 |
| 9,907,652 B2* | 3/2018 | Chau | A61F 2/246 |
| 10,123,874 B2* | 11/2018 | Khairkhahan | A61F 2/2466 |
| 10,166,098 B2 | 1/2019 | Khairkhahan et al. | |
| 10,226,341 B2* | 3/2019 | Gross | A61F 2/246 |
| 10,390,714 B2* | 8/2019 | Wolinsky | A61B 5/02152 |
| 10,449,046 B2* | 10/2019 | Rafiee | A61F 2/2457 |
| 10,470,883 B2 | 11/2019 | Khairkhahan et al. | |
| 10,478,303 B2* | 11/2019 | Khairkhahan | A61F 2/2445 |
| 10,500,048 B2* | 12/2019 | Khairkhahan | A61B 17/0401 |
| 10,512,542 B2* | 12/2019 | Khairkhahan | A61L 27/3625 |
| 10,702,386 B2 | 7/2020 | Khairkhahan et al. | |
| 11,000,372 B2* | 5/2021 | Khairkhahan | A61F 2/2463 |
| 11,083,572 B2* | 8/2021 | McLean | A61F 2/2412 |
| 11,344,410 B2* | 5/2022 | Hacohen | A61F 2/2409 |
| 11,633,281 B2* | 4/2023 | Kappetein | A61B 5/076 623/2.36 |
| 2003/0199975 A1 | 10/2003 | Gabbay | |
| 2004/0093060 A1 | 5/2004 | Sequin et al. | |
| 2007/0038297 A1 | 2/2007 | Bobo, Jr. et al. | |
| 2008/0077235 A1* | 3/2008 | Kirson | A61F 2/2418 623/2.11 |
| 2010/0217382 A1* | 8/2010 | Chau | A61F 2/2418 623/2.12 |
| 2010/0262233 A1* | 10/2010 | He | A61F 2/2454 623/2.41 |
| 2010/0280604 A1* | 11/2010 | Zipory | A61B 17/064 623/2.37 |
| 2011/0029072 A1* | 2/2011 | Gabbay | A61F 2/2418 623/2.37 |
| 2011/0276130 A1* | 11/2011 | Alameddine | A61F 2/2445 623/2.37 |
| 2012/0197388 A1* | 8/2012 | Khairkhahan | A61F 2/2466 623/2.11 |
| 2012/0197392 A1 | 8/2012 | DuMontelle et al. | |
| 2013/0006352 A1* | 1/2013 | Yaron | A61F 2/2427 623/2.37 |
| 2014/0067048 A1* | 3/2014 | Chau | A61F 2/2454 623/2.1 |
| 2014/0358223 A1 | 12/2014 | Rafiee et al. | |
| 2015/0119981 A1 | 4/2015 | Khairkhahan et al. | |
| 2015/0142104 A1 | 5/2015 | Braido | |
| 2015/0148893 A1* | 5/2015 | Braido | A61F 2/2412 623/2.4 |
| 2015/0230919 A1* | 8/2015 | Chau | A61F 2/2409 623/2.11 |
| 2015/0327996 A1 | 11/2015 | Fahim et al. | |
| 2016/0030176 A1 | 2/2016 | Mohl et al. | |
| 2016/0045165 A1 | 2/2016 | Braido et al. | |
| 2016/0045316 A1 | 2/2016 | Braido et al. | |
| 2016/0074164 A1* | 3/2016 | Naor | A61F 2/2409 623/2.11 |
| 2017/0065418 A1* | 3/2017 | Skarsgard | A61F 2/2487 |
| 2017/0095332 A1* | 4/2017 | Bruchman | A61F 2/2445 |
| 2017/0165067 A1 | 6/2017 | Barajas-Torres et al. | |
| 2017/0258589 A1* | 9/2017 | Pham | A61F 2/246 |
| 2017/0296706 A1* | 10/2017 | Simon | B01D 67/0072 |
| 2018/0143087 A1* | 5/2018 | Gouko | G01K 17/20 |
| 2018/0147054 A1* | 5/2018 | Chau | A61F 2/246 |
| 2018/0243087 A1* | 8/2018 | Kapadia | A61F 2/246 |
| 2018/0271651 A1 | 9/2018 | Christianson et al. | |
| 2018/0325666 A1 | 11/2018 | Ma | |
| 2019/0091047 A1 | 3/2019 | Walsh | |
| 2019/0201191 A1 | 7/2019 | McLean et al. | |
| 2020/0188108 A1 | 6/2020 | Grimm et al. | |
| 2020/0205978 A1 | 7/2020 | Padala et al. | |
| 2020/0222185 A1 | 7/2020 | Kappetein et al. | |
| 2020/0268512 A1 | 8/2020 | Mohl | |
| 2020/0289265 A1 | 9/2020 | Gifford, III et al. | |
| 2020/0360138 A1 | 11/2020 | Ma | |
| 2021/0307901 A1* | 10/2021 | Raanani | A61F 2/2436 |
| 2022/0039951 A1* | 2/2022 | Khairkhahan | A61F 2/2442 |
| 2022/0125579 A1* | 4/2022 | McLean | A61F 2/2454 |
| 2022/0125586 A1* | 4/2022 | Rafiee | A61F 2/2436 |
| 2022/0160508 A1* | 5/2022 | Miyashiro | A61F 2/246 |
| 2023/0040083 A1 | 2/2023 | Gifford, III et al. | |

FOREIGN PATENT DOCUMENTS

| | | |
|---|---|---|
| WO | 2004014258 A1 | 2/2004 |
| WO | 2005002424 A3 | 1/2005 |
| WO | 2012177942 A2 | 12/2012 |
| WO | 2014195422 A1 | 12/2014 |
| WO | 2014207575 A2 | 12/2014 |
| WO | 2015052570 A1 | 4/2015 |
| WO | 2017096157 A1 | 6/2017 |
| WO | 2018142186 A1 | 8/2018 |
| WO | 2019045910 A1 | 3/2019 |
| WO | 2020101676 A1 | 5/2020 |
| WO | 2021027588 A1 | 2/2021 |
| WO | 2021113449 A1 | 6/2021 |

OTHER PUBLICATIONS

ISA, PCT Application No. PCT/US2020/013953, International Search Report and Written Opinion dated Apr. 15, 2020, 14 pages.
ISA, PCT Application No. PCT/US2020/022471, International Search Report and Written Opinion dated Jun. 3, 2020, 17 pages.
ISA, PCT Application No. PCT/US2020/051887, International Search Report and Written Opinion dated Nov. 27, 2020, 13 pages.
Japanese Office Action Application No. 2020-534161, dated Sep. 5, 2022, 12 pages with translation.
Japanese Final Rejection Application No. 2020-534161, dated Jun. 12, 2023, 12 pages with translation.
ISA, PCT Application No. PCT/US2022/048999, International Search Report and Written Opinion dated Mar. 15, 2023, 23 pages.
Notice of Allowance U.S. Appl. No. 16/745,246 dated Dec. 22, 2022, 7 pages.
Notice of Allowance U.S. Appl. No. 16/817,464 dated Jul. 25, 2022, 14 pages.
Indian Office Action Application No. 202017013197, dated Dec. 9, 2022, 7 pages with translation.
Japanese Office Action Application No. 2021-526692, dated Nov. 16, 2022, 7 pages with translation.
Japanese Final Rejection Application No. 2021-526692, dated Jul. 20, 2023, 4 pages with translation.
Indian Office Action Application No. 202117026236, dated Jan. 20, 2023, 6 pages with translation.

* cited by examiner

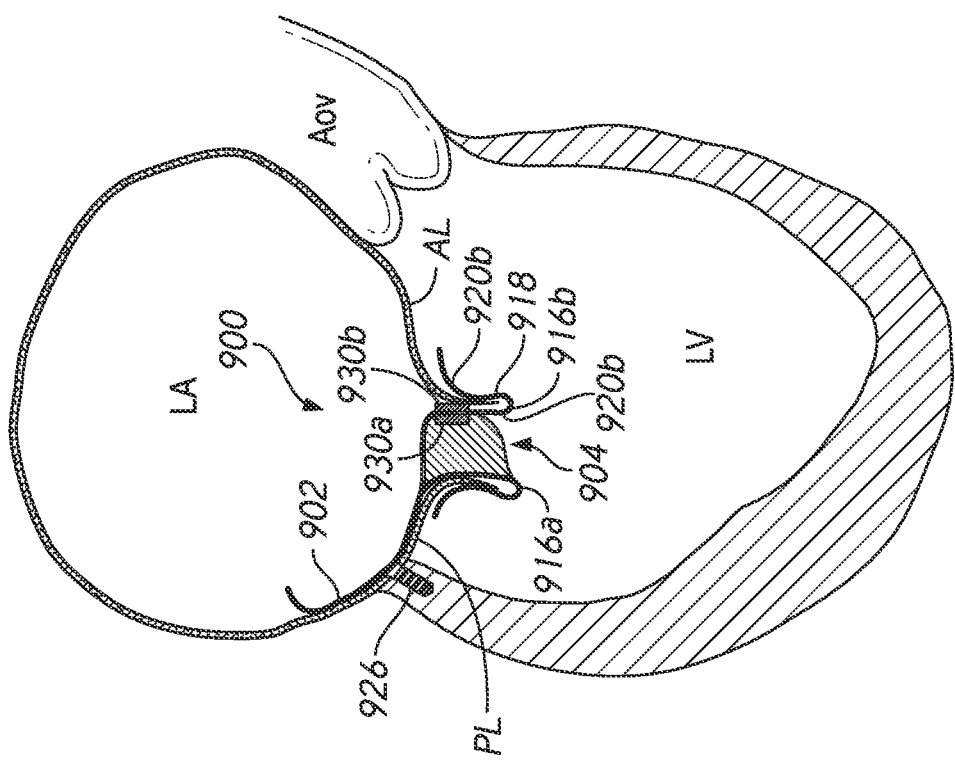
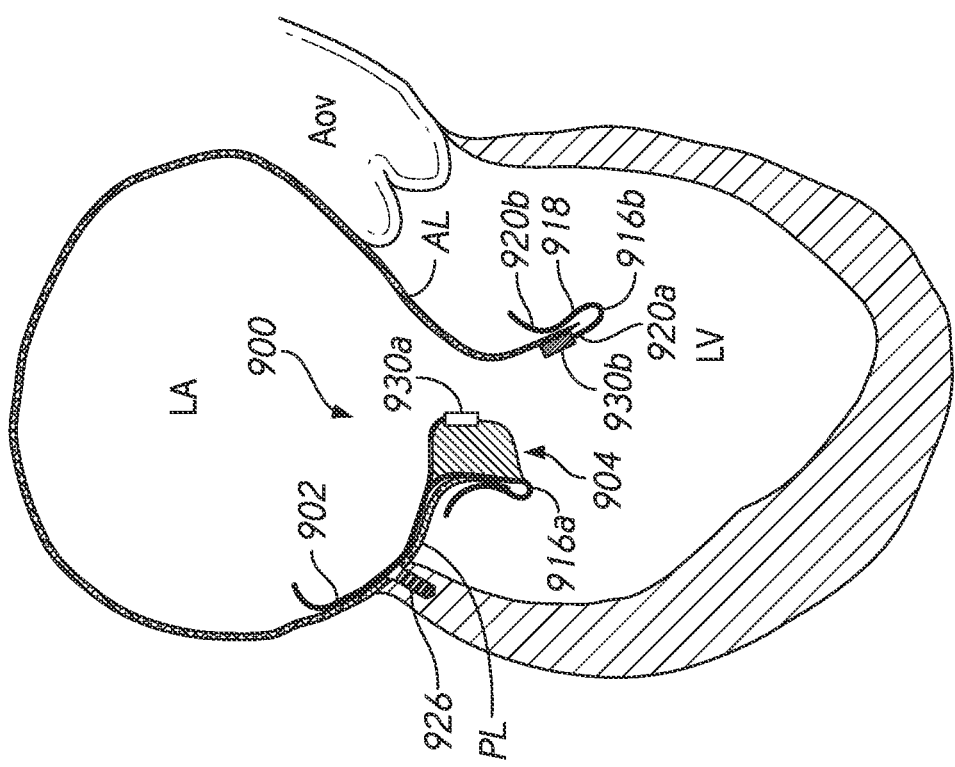
FIG. 9A
FIG. 9B

VALVE REPAIR DEVICES WITH COAPTATION STRUCTURES AND MULTIPLE LEAFLET CAPTURE CLIPS

CROSS-REFERENCE TO RELATED APPLICATION(S)

The application claims priority to and the benefit of U.S. Provisional Application No. 62/902,694, filed Sep. 19, 2019, which is incorporated herein by reference in its entirety.

TECHNICAL FIELD

The present technology is directed to devices, systems, and methods for cardiac valve repair, and more particularly to valve repair devices with coaptation structures and multiple leaflet capture clips.

INTRODUCTION

Proper functioning of the mitral valve can be affected by mitral valve regurgitation, mitral valve prolapse, and/or mitral valve stenosis. Mitral valve regurgitation can occur when the leaflets of the mitral valve fail to coapt into apposition at peak contraction pressures such that blood leaks from the left ventricle into the left atrium. Several structural factors may affect the proper closure of the mitral valve leaflets. For example, an enlarged mitral annulus caused by dilation of heart muscle may prevent proper coaptation of the leaflets during systole. Other conditions involve a stretch or tear in the chordae tendineae—the tendons connecting the papillary muscles to the inferior side of the mitral valve leaflets—which may also affect proper closure of the mitral annulus. A ruptured chordae tendineae, for example, may cause a valve leaflet to prolapse into the left atrium due to inadequate tension on the leaflet. Abnormal backflow can also occur when the papillary muscles are compromised (e.g., due to ischemia) such that the affected papillary muscles do not contract sufficiently to effect proper closure during systole.

Mitral valve prolapse can occur when the mitral leaflets abnormally bulge up in to the left atrium, which can also lead to mitral valve regurgitation. Normal functioning of the mitral valve may also be affected by mitral valve stenosis, or a narrowing of the mitral valve orifice, which impedes of filling of the left ventricle during diastole.

Mitral valve regurgitation is often treated using diuretics and/or vasodilators to reduce the amount of blood flowing back into the left atrium. Other treatment methods, such as surgical approaches (open and intravascular), have also been used to either repair or replace the native mitral valve. For example, cinching or resecting portions of the dilated annulus are typical repair approaches. Cinching of the annulus has been accomplished by implanting annular or peri-annular rings which are generally secured to the annulus or surrounding tissue. Other repair procedures have also involved suturing or clipping of the valve leaflets into partial apposition with one another. Alternatively, more invasive procedures replace the entire valve with mechanical valves or biological tissue. These invasive procedures are conventionally done through large open thoracotomies and are thus very painful, have significant morbidity, and require long recovery periods.

However, with many repair and replacement procedures, the durability of the devices or improper sizing of annuloplasty rings or replacement valves may cause complications. Moreover, many of the repair procedures depend upon the skill of the cardiac surgeon since poorly or inaccurately placed sutures may affect the success of procedures.

Compared to other cardiac valves, the mitral valve presents unique challenges because portions of the mitral valve annulus have limited radial support from surrounding tissue and the mitral valve has an irregular, unpredictable shape. For example, the anterior wall of the mitral valve is bound by only a thin wall separating the mitral valve annulus from the inferior portion of the aortic outflow tract. As a result, significant radial forces on the mitral valve annulus are not acceptable as they could lead to collapse of the inferior portion of the aortic tract with potentially fatal consequences. Another challenge of the mitral valve anatomy is that the maze of chordae tendineae in the left ventricle makes navigating and positioning a deployment catheter much more difficult compared to other heart valves. Given the difficulties and shortcomings associated with current procedures, there remains the need for simple, effective, and less invasive devices and methods for treating dysfunctional heart valves.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

FIGS. 9A and 9B are side cross-sectional views of a valve repair device shown before and after independent clip engagement, respectively, in accordance with embodiments of the present technology.

DETAILED DESCRIPTION

Figure 1A:
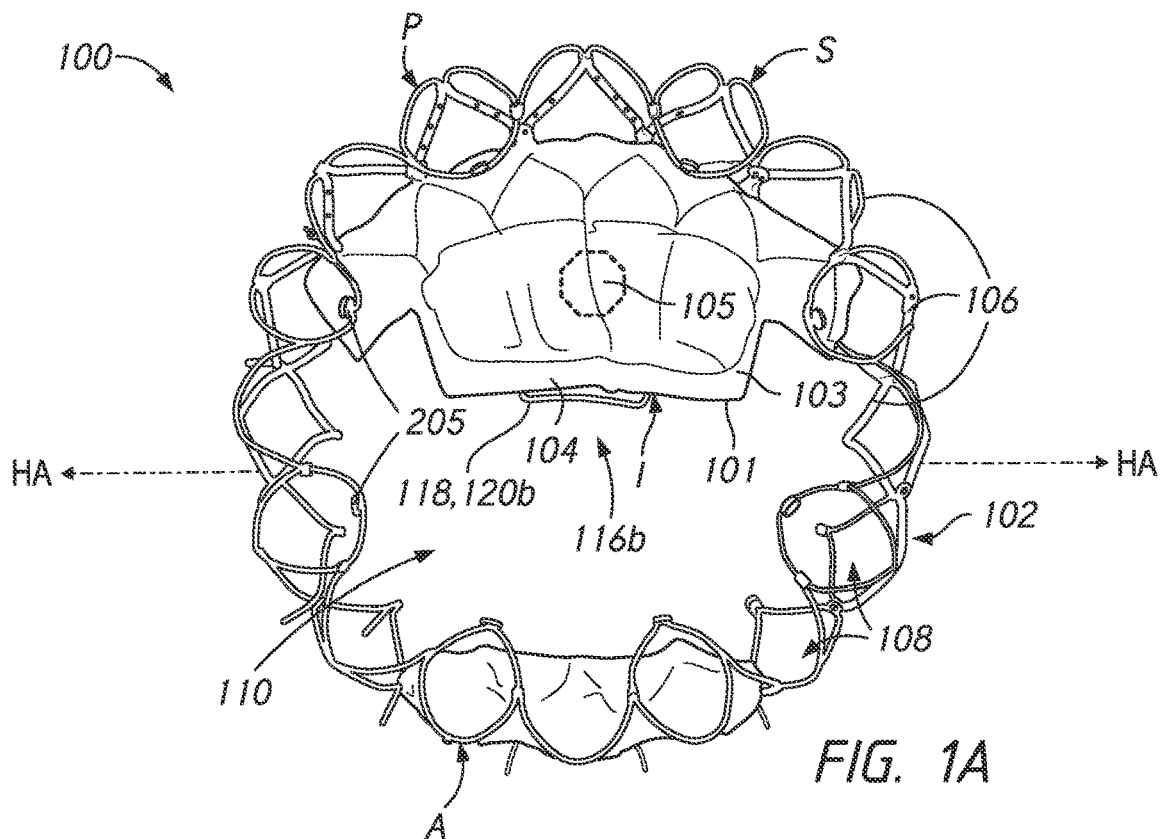
FIGS. 1A and 1B are top and side views, respectively, of a valve repair device configured in accordance with embodiments of the present technology.

The present technology is directed to a cardiac valve repair devices with coaptation structures and multiple clip mechanisms and associated systems and methods. In some embodiments, for example, cardiac valve repair devices (also referred to herein as "mitral valve repair devices," "coaptation assist devices," "implant devices," and iterations thereof) include: (i) a coaptation member (also referred to as a "coaptation structure," "baffle," "intravalvular body," "intermediate structure," and iterations thereof) positioned between native valve leaflets, and (ii) two or more clip mechanisms (also referred to as "clips," "capture clips," "capture mechanisms," and iterations thereof) that secure the coaptation member to one or more native leaflets (e.g., the posterior leaflet and/or the anterior leaflet of the mitral valve). The coaptation member may be coupled to a fixation member (also referred to as a "brim," "anchoring structure," "atrial fixation member," and iterations thereof) that anchors to cardiac tissue within the atrium and/or provides a platform for ingrowth to hold the coaptation member in place.

The coaptation member at least partially fills the regurgitant orifice in a leaking cardiac valve (e.g., the mitral valve) and provides a new coaptation surface for the native leaflets to seal around. The coaptation member can push a portion of the native leaflet (e.g., the P2 segment of the posterior leaflet of the native mitral valve) outward towards the ventricular wall, while reducing or minimizing disruption of the remaining native leaflets. In various embodiments, the transverse cross section of the coaptation member (i.e., the top view) may have an asymmetrical, crescent shape to correspond with the natural shape of the coaptation line of the mitral valve. In some embodiments, the coaptation member has other asymmetrical shapes that may correspond to the natural coaptation line of other valves or portions thereof. This shape is expected to provide more efficient leak reduction than a symmetric coaptation member, and is further expected to reduce the need for implanting multiple separate clip-like devices for proper coaptation, which is common in other clip procedures lacking a coaptation member (e.g., procedures using Mitraclip by Abbot Laboratories of Abbott Park, Illinois). For example, in the Mitraclip degenerative MR trials (EVEREST II and REALISM), 54% of the patients that received clips, received more than 1 (maximum of 2), while in the functional MR trial (COAPT), 64% of the 288 patients received more than 1 clip (maximum of 4).

When implanted at the mitral valve, the coaptation member can be rotationally oriented and stabilized at the central portion of the posterior leaflet (i.e., P2) via a sub-annular clip (also referred to herein as "primary clip," "first clip mechanism," and "posterior clip") that reaches under the native leaflet through the chordae-free zone near the center of P2. The valve repair device can include one or more additional clips that secure to different portions of the same leaflet as the primary clip, such as the lateral portion (P1) and/or medial portion (P3) of the posterior leaflet, and/or secure to other leaflets, such as the anterior leaflet. A secondary clip, for example, may be deployed to secure the coaptation member to the native anterior leaflet (such a secondary clip is also referred to herein as an "anterior clip," "second clip mechanism," and "A2 clip"). The anterior clip may be shorter than the primary clip to avoid it from extending up to the aortic valve and potentially disrupting aortic valve function. Alternatively, or in addition to the aforementioned anterior clip embodiments, the valve repair device can include a clip (e.g., a secondary clip or a tertiary clip) that is rotationally oriented with respect to the coaptation member so that the clip can be deployed at other portions of the posterior leaflet (e.g., P1 or P3) instead of a the anterior leaflet, depending on the shape, size, and location of the regurgitant orifice.

The fixation member can be positioned and deployed in the atrium after the coaptation member and clips have been deployed. In some embodiments, the fixation member is deployed before the coaptation member and/or one or more of the clips. The fixation member secures and stabilizes the coaptation member and provides a platform for tissue ingrowth. The additional stability provided by the fixation member may reduce or eliminate the need for frictional elements on the clips, thereby reducing or minimizing the impact on the native leaflets during clip deployment and positioning. Furthermore, the ingrown fixation member may provide an "annuloplasty" effect, limiting further expansion of the mitral annulus due to the fibrous tissue incorporation.

Specific details of several embodiments of the technology are described below with reference to FIGS. 1A-10. Although many of the embodiments are described below with respect to implant devices, systems, and methods for repair of a native mitral valve, other applications and other embodiments in addition to those described herein are within the scope of the technology. For example, the present technology may be used at other target sites, like the tricuspid valve, the pulmonary valve, and/or the aortic valve. Additionally, several other embodiments of the technology can have different configurations, components, or procedures than those described herein, and features of the embodiments shown can be combined with one another. A person of ordinary skill in the art, therefore, will accordingly understand that the technology can have other embodiments with additional elements, or the technology can have other embodiments without several of the features shown and described below with reference to FIGS. 1A-10. In some instances, well-known structures and techniques often associated with cardiac implants and prosthetic heart valves have not been shown in detail so as not to obscure the present technology. The terminology used in the description presented below is intended to be interpreted in its broadest reasonable manner, even though it is being used in conjunction with a detailed description of certain specific embodiments of the disclosure.

The accompanying Figures depict embodiments of the present technology and are not intended to be limiting of its scope. The sizes of various depicted elements are not necessarily drawn to scale, and these various elements can be arbitrarily enlarged to improve legibility. Component details can be abstracted in the Figures to exclude details such as position of components and certain precise connections between such components when such details are unnecessary for a complete understanding of how to make and use the present technology. Many of the details, dimensions, angles, and other features shown in the Figures are merely illustrative of particular embodiments of the disclosure. Accordingly, other embodiments can have other details, dimensions, angles, and features without departing from the spirit or scope of the present technology.

With regard to the terms "distal" and "proximal" within this description, unless otherwise specified, the terms can reference a relative position of the portions of a catheter subsystem with reference to an operator and/or a location in the vasculature. Also, as used herein, the designations "rearward," "forward," "upward," "downward," etc., are not meant to limit the referenced component to use in a specific orientation. It will be appreciated that such designations refer to the orientation of the referenced component as illustrated in the Figures; the systems of the present technology can be used in any orientation suitable to the user.

With regard to the terms "distal" and "proximal" within this description, unless otherwise specified, the terms can reference a relative position of the portions of a valve repair device and/or an associated delivery device with respect to an operator and/or a location in the vasculature or heart. For example, in referring to a delivery catheter suitable to deliver and position various valve repair devices described herein, "proximal" can refer to a position closer to the operator of the device or an incision into the vasculature, and "distal" can refer to a position that is more distant from the operator of the device or further from the incision along the vasculature (e.g., the end of the catheter). With respect to a heart valve repair device, the terms "proximal" and "distal" can refer to portions of the device relative to the native annulus. For example, "proximal" can refer to an upstream portion of the device spaced apart from the native annulus, and "distal" can refer to a downstream position at or proximate to the native annulus.

Further, as used herein, the designations "forward," "rearward," "upward," "downward," "top," "bottom," etc., are not meant to limit the referenced component to use in a specific orientation. It will be appreciated that such designations refer to the orientation of the referenced component as illustrated in the Figures. However, the systems of the present technology can be used in any orientation suitable to the user.

The headings provided herein are for convenience only and should not be construed as limiting the subject matter disclosed.

Selected Embodiments of Valve Repair Devices

Figure 1B:
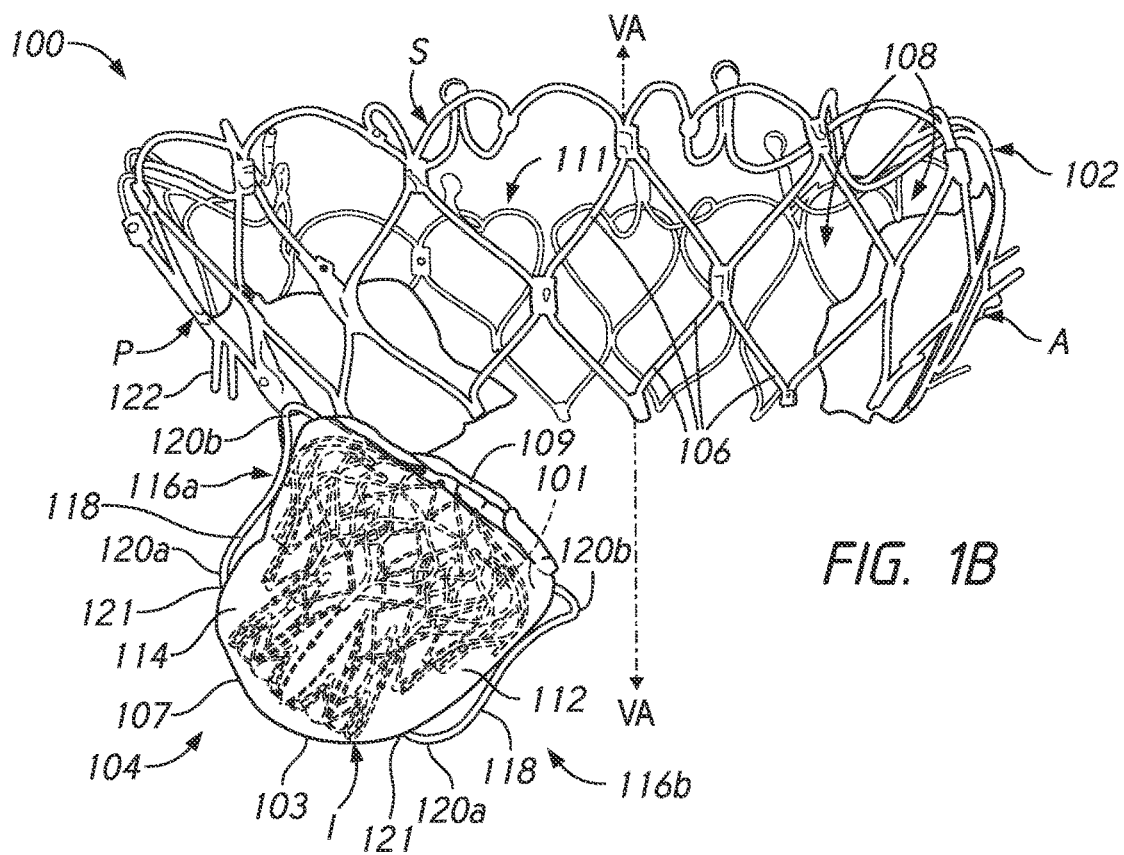
Figure 1D:
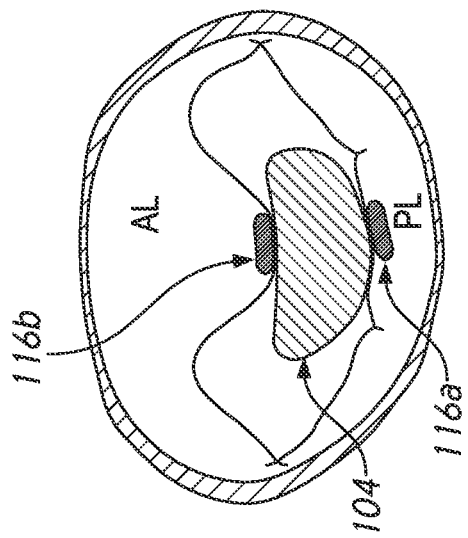
FIGS. 1D and 1E are transverse cross-sectional views of the valve repair device of FIGS. 1A-1C during diastole and systole, respectively, in accordance with embodiments of the present technology.
Figure 1E:
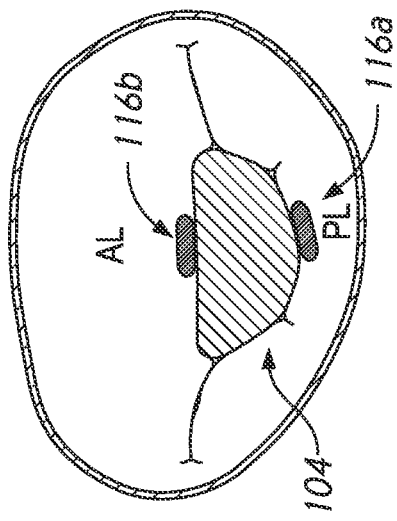
Figure 1C:
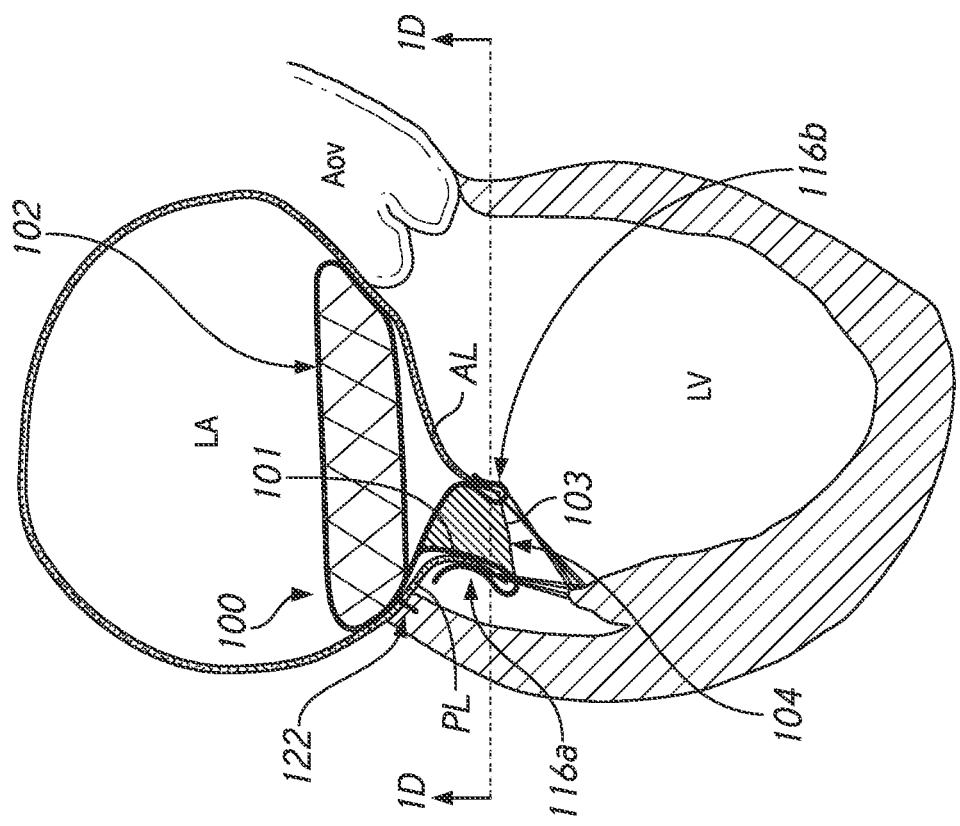
FIG. 1C is a side cross-sectional view of the valve repair device of FIGS. 1A and 1B implanted at a mitral valve in accordance with embodiments of the present technology.

FIGS. 1A and 1B are top and side views, respectively, of a valve repair device 100 ("device 100") that may be implanted in a heart of a subject (e.g., a human patient) in accordance with embodiments of the present technology. FIGS. 1C-1E are side and transverse cross-sectional views of the device 100 of FIGS. 1A and 1B implanted at a mitral valve in accordance with embodiments of the present technology. Referring to FIGS. 1A and 1B together, the device 100 can include a fixation member 102, a coaptation member 104 extending from the fixation member 102 in a downstream direction, and a plurality of clip mechanisms (identified individually as a first clip mechanism 116a and a second clip mechanism 116b; referred to collectively as "clip mechanisms 116") depending from the coaptation member 104. The fixation member 102 is sized and shaped to anchor the device 100 to cardiac tissue proximate to or upstream of a native valve annulus (e.g., atrial tissue), and positions the coaptation member 104 between native valve leaflets at a desired location with respect to the native valve anatomy of the heart. The coaptation member 104 has a volume that fills at least a portion of the regurgitant orifice between the native leaflets, may displace at least a portion of one or more native leaflets, and provides a prosthetic coaptation surface for at least a portion of one or more of the native leaflets of the cardiac valve. For example, as shown in FIGS. 1C-1E, when the device 100 is deployed across the mitral valve annulus, the coaptation member 104 may extend in front of a central portion of the posterior leaflet PL (i.e., P2 of the posterior leaflet PL) to position the coaptation member 104 in a location that allows it to coapt with the anterior leaflet AL during systole (FIG. 1E). The clip mechanisms 116 are configured to extend behind and grasp portions of one or more native leaflets to affix the one or more leaflets to the coaptation member 104.

As shown in FIGS. 1A and 1B, the device 100 is configured relative to a flow axis VA (FIG. 1B) in the direction of blood flow from the atrium to the ventricle and a transverse axis HA (FIG. 1A) at an angle (e.g., orthogonal) to the flow axis VA. The device 100 has a first side P (e.g., a posterior side), a second side A (e.g., an anterior side) opposite the first side P, a superior end portion S (e.g., a first end portion), and an inferior end portion I (e.g., a second end portion) opposite the superior end portion S.

In some embodiments, the device 100 can include some features generally similar or identical to the implantable devices described in (i) U.S. patent application Ser. No. 16/044,447, titled "PROSTHETIC LEAFLET DEVICE," and filed Jul. 24, 2018, (ii) International Patent Application No. PCT/US2018/061126, titled "LEAFLET EXTENSION FOR CARDIAC VALVE LEAFLET," and filed Nov. 14, 2018, (iii) U.S. patent application Ser. No. 16/745,246, titled "IMPLANTABLE COAPTATION ASSIST DEVICES WITH SENSORS AND ASSOCIATED SYSTEMS AND METHODS," and filed Jan. 16, 2020, and/or (iv) U.S. patent application Ser. No. 16/817,464, titled "CARDIAC VALVE REPAIR DEVICES WITH ANNULOPLASTY FEATURES AND ASSOCIATED SYSTEMS AND METHODS," and filed Mar. 12, 2020, each of which is incorporated herein by reference in its entirety. Any of the valve repair devices disclosed herein can be delivered to a cardiac valve intravascularly (e.g., trans-septal delivery via the femoral or axial vein), percutaneously (e.g., transapically), and/or surgically.

The fixation member 102 can be formed of a mesh, such as a braid or laser-cut stent-like structure, and/or other type of frame including a plurality of interconnected wires or struts 106 that together define a plurality of openings or cells 108 (e.g., diamond-shaped openings) arranged in one or more rows. The struts 106 can be configured to self-expand from a collapsed delivery state (not shown) to an expanded deployed state shown in FIGS. 1A and 1B. The struts 106 can be made from any biocompatible material such as, for example, stainless steel, nickel-titanium alloys (e.g., nitinol), and/or other suitable stent materials. The fixation member 102 can have a generally circular, oval, or D-like shape in the deployed state and define an open central lumen 110 (also referred to as an "opening 110") that allows blood to pass therethrough along the flow axis VA. When the device 100 is configured to repair a native mitral valve, the fixation member 102 can be shaped to conform to the walls of the left atrium just above the mitral annulus to secure the device 100 to the supra-annular tissue. After a period of time post-implantation (e.g., 3 days, 2 weeks, 1 month, 2 months), the fixation member 102 or portions thereof become covered by a layer of tissue, and this tissue ingrowth adheres the device 100 permanently to the atrial wall. As described in further detail below, in some embodiments the fixation member 102 has a semicircular or other shape that does not extend fully around the circumference of the native valve. In some embodiments, the fixation member 102 may also or alternatively include one or more portions that extend into the annulus and/or press against sub-annular tissue to provide sub-annular device fixation.

As shown in FIG. 1B, in some embodiments the fixation member 102 includes additional fixation elements 122 along projecting outwardly from the fixation member 102 and configured to enhance anchoring and/or stimulate tissue ingrowth. The frictional elements 122 can be tines, barbs, prongs, screws, hooks, corrugations, and/or other features or structures that enhance tissue engagement. In the illustrated embodiment, for example, the frictional elements 122 include two prongs extending outwardly in a downstream direction from an inferior portion of the fixation member so that they can project into tissue near the annulus. In other embodiments, the fixation member 102 can include additional and/or different frictional elements 122.

As shown in FIGS. 1A and 1B, the coaptation member 104 extends away from a downstream portion of the fixation member 102 along the flow axis VA and at least a portion of the coaptation member 104 extends radially inward from the fixation member 102 into the central lumen 110 to fill a portion of the native valve orifice. In the illustrated embodiment, the coaptation member 104 is angled or biased outwardly from the central valve axis (e.g., in a posterior direction) to push a portion of the adjacent native leaflet back from the valve opening and approximate a closed position of the native leaflet. In some embodiments, the coaptation member 104 is more centrally located within the valve orifice. The coaptation member 104 can be substantially stationary (e.g., little to no movement) during cardiac cycles such that the position of the coaptation member 104 relative to the fixation member 102 is at least substantially fixed in the deployed state. Thus, unlike native leaflets that move back and forth to open and close the native valve, the coaptation member 104 remains stationary during diastole and systole. In some embodiments, the coaptation member 104 does undergo some movement during cardiac cycling, though not to the same extent as native leaflets.

The coaptation member 104 has an inner portion 112 (FIG. 1B; also referred to as a "first portion," "anterior portion," "side," or "surface") facing the central axis of the valve and toward one or more opposing valve leaflets, an outer portion 114 (FIG. 1B; also referred to as a "second portion," "posterior portion," "side," or "surface") facing away from the central axis of the valve, a downstream end portion 107 (also referred to as a "bottom portion" or an "inferior portion"), and an upstream end portion 109 (also referred to as a "top portion," "lid," or "superior portion"). The inner portion 112 may have a smooth, atraumatic surface 113 (also referred to as a "coaptation surface") for coapting with at least a portion of one or more opposing native leaflets, whereas the outer portion 114 may displace and engage at least a portion of another native leaflet. In some embodiments, the inner portion 112 and/or the outer portion 114 may include friction elements that engage the native leaflets.

The coaptation member 104 includes an expandable frame structure 101 (e.g., a mesh structure, a laser cut stent frame) made from a plurality of connected struts (e.g., similar to the struts 106 of the fixation member 102) that define an at least partially hollow interior space when the device 100 is in the deployed state. In some embodiments, for example, the frame structure 101 may include interconnected struts extending along the inner portion 112 and the outer portion 114 (e.g., elongated struts or a mesh-like structure), and elongated struts extending along the downstream end portion 107 and the upstream end portion 109. Portions of the frame structure 101 may be disconnected (e.g., at the downstream end portion 107) allowing portions of the struts to slide over one another and/or move apart from each other to facilitate a low profile in the delivery state and/or adjustability of the coaptation member 104 dimensions. The coaptation member 104 or portions thereof can be integral with the fixation member 102. For example, struts 106 from the fixation member 102 can extend in a downstream direction to define a portion of the frame structure 101. In other embodiments, the coaptation member 104 is a separate structure that is connected to a portion of the fixation member 102 during manufacturing using welding, adhesives, connectors, and/or other suitable connection mechanisms.

A covering 103 (e.g., fabric, graft material) can extend over at least a portion of the frame structure 101 to at least partially enclose the frame structure 101 and provide a smooth, atraumatic surface for contacting with the native leaflets pressed thereto or coapting therewith. In some embodiments, the covering 103 includes padded portions (e.g., a biocompatible foam), and/or a biocompatible foam may be attached to the frame structure 101. The covering 103 may extend over the struts along inner portion 112 and the outer portion 114 of the coaptation member 104, as well as between the inner and outer portions 112, 114 in a manner that forms lateral sidewalls. In some embodiments, the covering 103 may also extend between the inner and outer portions 112, 114 along the downstream end portion 107 and/or the upstream end portion 109 such that the frame structure 101 and covering 103 together form an enclosed cavity with an interior volume. The covering 103 may include one or more access openings 105, such as a slit, valve, or hole in the covering 103, that provide access to the interior of the frame structure 101 and components therein during delivery and/or retrieval. For example, the opening 105 may provide access to delivery system connectors that allow for manipulation of the coaptation member and/or clip actuation mechanisms for opening and closing the clip mechanisms 116. Further, the cavity of the coaptation member 104 may house extension members, supplemental clips, and/or other components that may be optionally deployed during implant procedures.

The construction of the coaptation member 104, in particular the stent-like structure of the frame 101, lends itself to adjustability of the coaptation member dimensions compared to the other clipping devices with/without a filler. In some embodiments, the coaptation member 104 can be adjustable in width (along the transverse axis HA) and/or protrusion depth (the extent to which it fills the valve orifice). This adjustability could be enabled with insertable or removable elements inserted into the body of the coaptation member 104, such as axial rods, that expand/retract the stent-structure of the coaptation member 104 as they are inserted/removed. In some embodiments, the coaptation member 104 is divided to include partial or complete sections that are inflatable and/or passively swell to fill the regurgitant area. Suitable baffle structures, including adjustable baffles, are described in International Patent Application No. PCT/US2018/043566, filed Jul. 24, 2018, and International Patent Application No. PCT/US2018/061126, filed Nov. 14, 2018.

The clip mechanisms 116 extend from the inner portion 112 and/or the outer portion 114 of the coaptation member 104 to allow the clip mechanisms 116 to extend behind and capture the native leaflets positioned on one or both sides of the coaptation member 104. The clip mechanism 116 includes a base portion 120a (also referred to as a "first portion") affixed to the coaptation member 104, a free end portion 120b (also referred to as a "second portion") unaffixed to the coaptation member 104, and an articulatable arm member 118 that extends from the base portion 120a and forms the free end portion 102b. The base portion 120a can be attached at the downstream end portion 107 of the coaptation member 104 (e.g., to the frame structure 101 and/or the associated covering 103) by welding, adhesives, sutures, and/or other coupling mechanisms. In some embodiments, the base portion 120a may extend from the downstream end portion 107 in an upstream direction (i.e., in the direction of the flow axis VA) along the inner side or outer side of the coaptation member 104 (depending upon the clip location) to provide additional fixation to the coaptation member 104 and/or provide additional torque for actuating the arm member 118. The arm 118 can extend from the base portion 120a in an upstream direction (i.e., toward the fixation member 102) along a length of the coaptation member 104. For example, the arm member 118 may only extend partway up the coaptation member 104 and along the length of the coaptation member 104 to the downstream end of the fixation member 102. The arm 118 may form an inverted U-like shape and flare outwardly to form a wider section where the arm 118 clamps against the native leaflet. In other embodiments, the arm member 118 may have other suitable shapes for engaging leaflets and/or may include extensions at the distal-most end that engage sub-annular tissue for additional sub-annular stabilization and fixation.

The arm member 118 may be made from one or more wires, struts, and/or other semi-rigid/rigid structures with sufficient rigidity to clamp against the leaflet and/or sub-annular tissue. In some embodiments, the arm member 118 includes a fabric covering, a biocompatible foam or other type of padding, and/or a coating on the rigid member to provide a smooth surface to reduce trauma to the leaflets and/or surrounding tissue, additional surface area for leaflet engagement, and/or a platform for tissue ingrowth. In some embodiments, the arm member 118 and/or other portions of the clip mechanism 116 may have some spikes, tines, corrugations, or other frictional features that enhance the stability and fixation to the native leaflet.

The clip mechanism 116 can further include an actuation mechanism 121, such as a spring-loaded lever, that acts on the arm member 118 to move it between a closed position (shown in FIGS. 1A-1E; also referred to as a "closed state," "closed configuration," or "first state") and an open position (also referred to as an "open state," "open configuration," or "second state"). In the closed state, the arm member 118 is positioned close to or against the surface of the coaptation member 104, with at least a portion of the arm member 118 pressed against the surface of the coaptation member 104 to provide for leaflet engagement. In the open state, the articulatable arm member 118 extends away from the coaptation member 104 (e.g., forming a V-shape or L-shape with the surface portions 112 or 114) to allow the free end portion 120b to extend behind a native leaflet and receive the native leaflet between the arm member 118 and the surface of the coaptation member 104. In some embodiments, the actuation mechanism 121 holds the clip mechanism 116 in a normally closed state (e.g., due to a spring force) such that the clip mechanism 116 is in the closed state during device delivery and manipulation of the actuation mechanism 121 (e.g., pulling on the tendon) moves the clip mechanism 116 to the open state. In other embodiments, the clip mechanism 116 is arranged in a normally open state.

The actuation mechanism 121 can be a spring-loaded lever (e.g., a nitinol wire, laser cut nitinol or Co—Cr sheet) operably coupled to a portion of a delivery system (not shown) that can be manipulated to move the clip mechanism 116 between the open and closed positions. For example, a flexible tendon (made of suture or nitinol wire) can be attached to the spring-loaded lever, extend alongside or through the body of the coaptation member 104 (passing through the opening 105 (FIG. 1A)), and through a delivery catheter to an external handle assembly. A clinician can pull on or otherwise apply tension to the tendon, which translates this force to the lever, thereby moving the arm member 118 between the closed and open positions. In other embodiments, the actuation mechanism 121 may have different actuation means, such as other springs, clamps, pulleys, interfacing threaded members, and/or further actuation mechanisms described in International Patent Application No. PCT/US2018/061126, filed Nov. 14, 2018. Further, because each clip mechanism 116 includes its own actuation mechanism 121, the clip mechanisms 116 can be independently actuated.

In the illustrated embodiment, the first clip mechanism 116a depends from the outer portion 114 of the coaptation member 104 and the second clip mechanism 116b depends from the inner portion 112 of the coaptation member 104 such that the two clip mechanisms 116 engage portions of opposing native leaflets. For example, when in the mitral valve (e.g., as shown in FIG. 1C-1E) the first clip mechanism 116a can reach under and grasp the central portion (i.e., P2) of the posterior leaflet PL, and the second clip mechanism 116b can reach under and grasp the central portion (i.e., A2) of the atrial leaflet AL. In some embodiments, the device 100 includes more than two clip mechanisms 116 and/or one of the clip mechanisms 116 may be omitted. In some embodiments, for example, the device 100 includes additional clip mechanisms 116 on the same side as the first clip mechanism 116a and/or on the same side as the second clip mechanism 116b to engage laterally spaced apart portions of the same native leaflet.

During a delivery procedure at the mitral valve, the device 100 may be placed in a compacted delivery state within a delivery catheter (not shown) and inserted through the vasculature (e.g., via a femoral vein) to traverse the inferior vena cava to the right atrium. The device 100 is then inserted into the left atrium via a puncture of the interatrial septum. The device 100 can be appropriately oriented with respect to the flow axis VA (FIG. 1B) and the transverse axis (FIG. 1A), and may also be rotationally and angularly oriented with respect to specific landmarks. For example, the device 100 can be oriented to align the clip mechanisms 116 with the desired portions of the native leaflets. In some embodiments, the device 100 may also be repositioned during the delivery process to, for example, correct for misalignment or inappropriate positioning. During deployment and release of the device 100, the delivery system can retain the device 100 in a desired orientation and location within the valve annulus. Furthermore, the delivery system may be configured to allow the device 100 to be re-sheathed, repositioned, and/or removed before being fully released from the delivery system. In several embodiments, the device 100 can be configured to be deployed via a delivery catheter with a small overall diameter, such as approximately 15 to 30 French.

Referring to FIGS. 1C-1E, when the device 100 is appropriately oriented within the valve orifice between the anterior and posterior leaflets AL, PL, the device 100 can be deployed from the delivery catheter. For example, deployment can begin by expanding the coaptation member 104 to fill at least a portion of the valve orifice. As shown in FIG. 1C, in some embodiments, expansion of the coaptation member 104 displaces at least a portion of the posterior leaflet PL. The clip mechanisms 116 can then be selectively activated to engage portions of the native leaflets. The first clip mechanism 116a can be placed in the open state (e.g., by pulling on a tendon coupled to a spring-loaded lever) to allow the arm member 118 to extend behind a portion of the posterior leaflet PL. With the posterior leaflet PL positioned between the arm member 118 and the outer portion 114 of the coaptation member 104, the first clip mechanism 116a can be moved to the closed state (e.g., by releasing the tensile force applied to the lever) such that the arm member 118 applies pressure and clamps against the back side of the posterior leaflet PL. Similarly, the second clip mechanism 116b can be placed in the open state (e.g., by pulling on a tendon coupled to a spring-loaded lever) to allow the arm member 118 to extend behind a portion of the anterior leaflet AL. With the anterior leaflet AL positioned between the arm member 118 and the inner portion 112 of the coaptation member 104, the second clip mechanism 116a can moved to the closed state (e.g., by releasing the tensile force applied to the lever) such that the arm member 118 applies pressure and clamps against the back side of the anterior leaflet AL. As shown in FIGS. 1D and 1E, the first and second clip mechanisms 116a and 116b capture central portions of the posterior leaflet PL and the anterior leaflet AL (P2 and A2), respectively. In these and other embodiments, the clip mechanisms 116 can capture different and/or additional portions of the native leaflets (e.g., lateral leaflet portions). In some embodiments, one or more of the clip mechanisms 116 may also include features that engage sub-annular cardiac tissue (e.g., the underside of the annulus or ventricular wall) for additional sub-annular stabilization of the device 100.

The delivery procedure can continue by deploying the fixation member 102 within the atrium. As the fixation member 102 expands, it contacts and engages supra-annular tissue along the atrial wall to provide supra-annular fixation for the device 100. As shown in FIG. 1C, the frictional elements 122 can extend into tissue near the posterior portion of the annulus to provide additional fixation. In some embodiments, the fixation member 102 is deployed in advance of the coaptation member 104 and/or the clip mechanisms 116.

After implantation, device 100 is expected to provide improved sealing during systole to reduce or eliminate valve regurgitation and provide for proper valve function. That is, the coaptation member 104 can fill a portion of the regurgitant valve orifice and the clip mechanisms 116 can draw portions of the leaflets inward such that they can coapt properly against each other and/or against the outer surface of the coaptation member 104. FIGS. 1D and 1E, for example, are transverse cross-sectional views (viewed from the ventricle) illustrating the implanted device 100 during diastole and systole, respectively. During diastole (FIG. 1D), the coaptation member 104 fills a portion of the mitral valve, and the clip mechanisms 116 draw in the central portions (P2 and A2) of the posterior leaflet PL and the anterior leaflet AL such that they are clamped against the coaptation member. The lateral portions of the posterior and anterior leaflet PL, AL remain free to relax and separate from each other, thereby opening the valve and allowing blood to flow therethrough. During systole (FIG. 1E), the posterior and anterior leaflets PL, AL move inward to coapt against the exterior surface of the coaptation member 104 and, where not clipped, the leaflets can coapt against each other. The multiple clips 116 aided by the coaptation member 104 can provide for improved sealing in patients with challenging anatomy (e.g., large regurgitant orifice, P1 or P3 prolapse, anterior leaflet prolapse) and/or anatomy that alters over time. In various embodiments, the device 100 can include additional or other clipping mechanisms 116 that draw in additional or different portions of the native leaflets to provide for proper coaptation. In these and other embodiments, the coaptation member 104 may extend along a longer portion or a shorter portion of the coaptation line (e.g., between the posterior commissure and the anterior commissure) and/or have a different cross-sectional shape to facilitate proper coaptation for the specific valve anatomy.

Figure 2B:
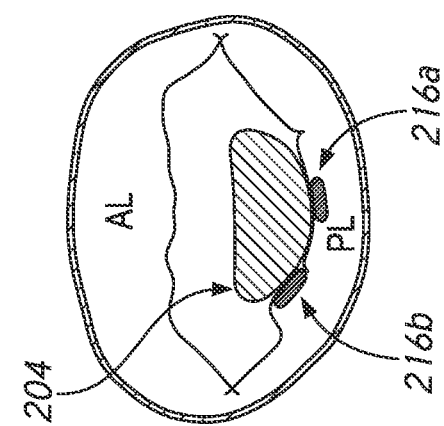
FIGS. 2B and 2C are side cross-sectional views of the valve repair device of FIG. 2A during diastole and systole, respectively, in accordance with embodiments of the present technology.
Figure 2C:
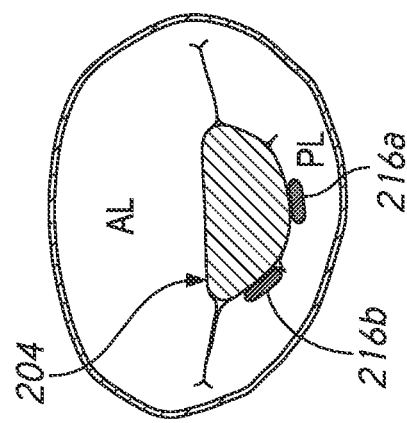
Figure 2A:
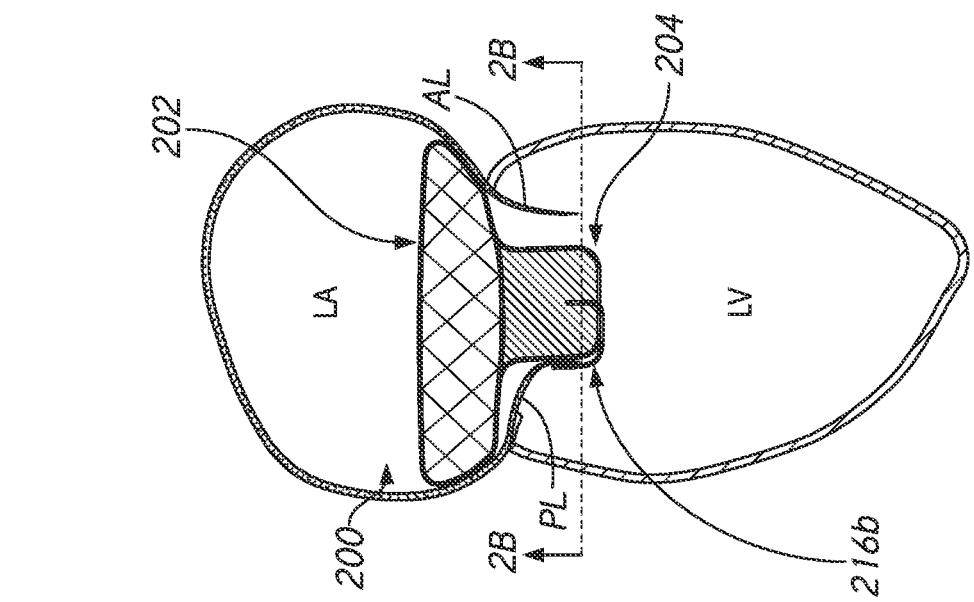
FIG. 2A is a side cross-sectional view of a valve repair device implanted at a mitral valve in accordance with embodiments of the present technology.

FIG. 2A is a side cross-sectional view of a valve repair device 200 ("device 200") implanted at a mitral valve in accordance with embodiments of the present technology, and FIGS. 2B and 2C are side cross-sectional views of the device 200 of FIG. 2A during diastole and systole, respectively. The device 200 can include various features at least generally similar to the features of the device 100 described above with respect to FIGS. 1A-1E. For example, the device 200 includes a fixation member 202 for engaging at least a portion of the atrial wall, a coaptation member 204 depending from the fixation member 202 and configured to be positioned between the native leaflets (e.g., extending in front of the posterior leaflet PL), and a plurality of clip mechanisms 216 (identified individually as a first clip mechanism 216a and a second clip mechanism 216b) configured to extend behind and engage portions of the native leaflets. In the illustrated embodiment, both of the clip mechanisms 216 are positioned on the outer portion of the coaptation member 204 such that they engage different portions of the same native leaflet. As shown in FIGS. 2B and 2C, for example, the first clip mechanism 216a engages the central portion (P2) of the posterior leaflet PL, and the second clip mechanism 216b engages a lateral portion (e.g., P3) of the posterior leaflet PL. In this embodiment, the device 200 does not include a clip associated with the anterior leaflet AL. Instead, the stability provided by the laterally spaced apart clip mechanisms 216 provides the necessary sub-annular fixation. In other embodiments, the device 200 may include clip mechanisms on additional portions of the same native leaflet (e.g., the posterior leaflet PL) and/or along one or more portions of an opposing leaflet (e.g., the anterior leaflet AL).

Figure 3A:
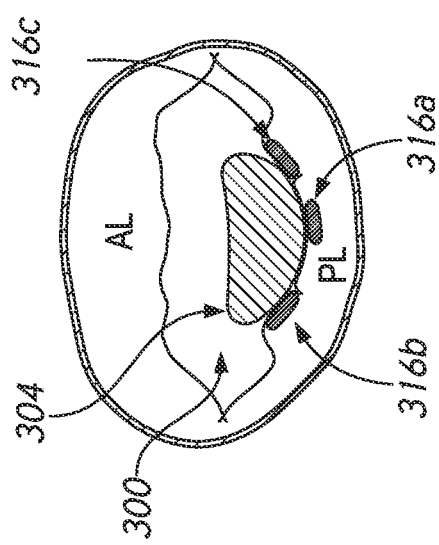
FIGS. 3A and 3B are side cross-sectional views of a valve repair device implanted at a mitral valve during diastole and systole, respectively, in accordance with embodiments of the present technology.
Figure 3B:
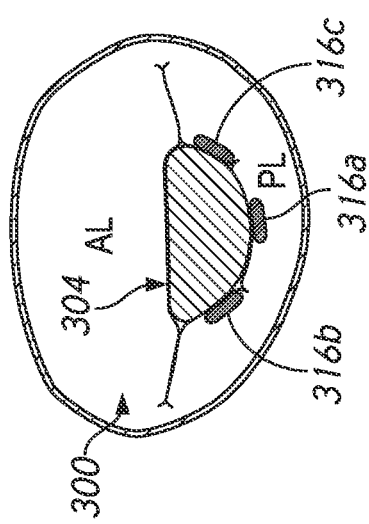
Figure 4:
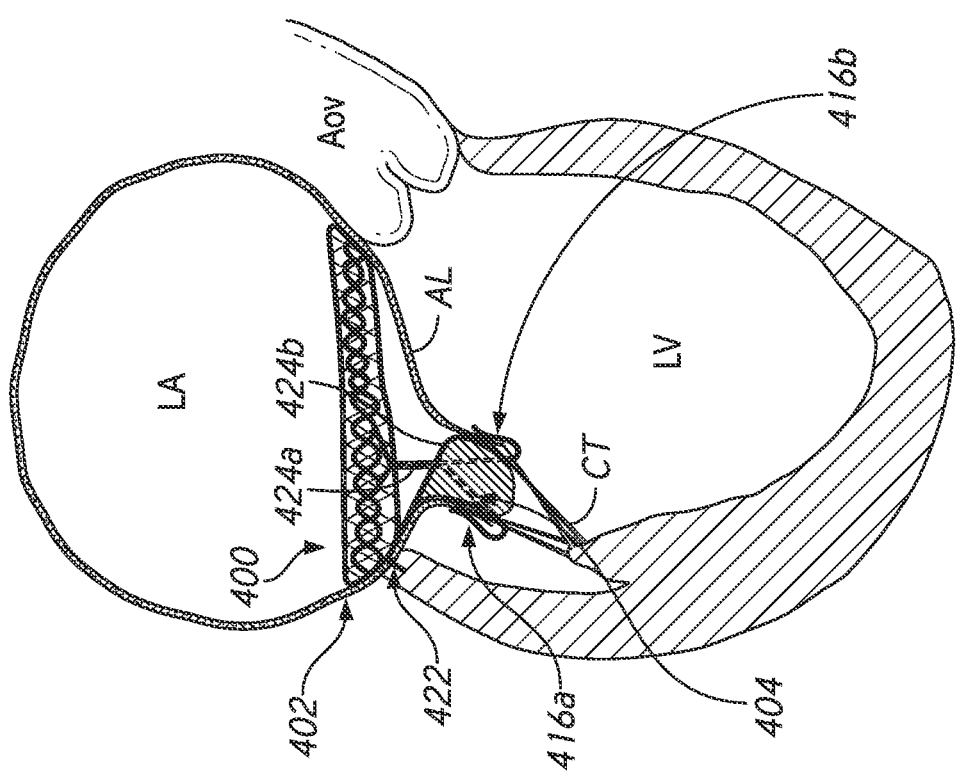
FIG. 4 is a side cross-sectional view of a valve repair device with a low-profile fixation member implanted at a mitral valve in accordance with embodiments of the present technology.

FIGS. 3A and 3B are side cross-sectional views of a valve repair device 300 ("device 300") within a mitral valve during diastole and systole, respectively, in accordance with embodiments of the present technology. The device 300 can include various features at least generally similar to the features of the device 200 described above with respect to FIGS. 2A-2C. For example, the device 300 can include an optional fixation member (not shown; e.g., the fixation members 102, 202 described above), a coaptation member 304 configured to be positioned between opposing native leaflets (e.g., extending in front of the posterior leaflet PL), and a plurality of clip mechanisms 316 (identified individually as a first clip mechanism 316a, a second clip mechanism 316b, and a third clip mechanism 316c) configured to engage different laterally spaced apart portions of the same native leaflet. In the illustrated embodiment, the device 300 includes three clip mechanisms 316 positioned on the same side of the coaptation member 304 and laterally spaced apart from each other. As shown in FIGS. 3A and 3B, for example, the first clip mechanism 316a can engage the central portion (P2) of the posterior leaflet PL, and the second clip mechanism 316b can engage a lateral portion (e.g., P3) of the posterior leaflet PL, and the third clip mechanism 316c can engage a different lateral portion (e.g., P1) of the posterior leaflet PL. The addition of the tertiary clip mechanism 316c provides leaflet support at each scallop of the posterior leaflet PL, drawing it into close engagement with the outer side of the coaptation member 304 without residual clefts. The combination of the coaptation member 304 spanning the posterior leaflet PL (in part or in whole) and three clip mechanisms 316 providing leaflet support at each scallop may provide sufficient fixation to obviate the need for a fixation member (whole or partial). In some embodiments, for example, the fixation member may be omitted. In some embodiments, the device 300 can include a partial fixation member that only extends along a non-circumferential portion of the atrium (e.g., a semicircular fixation structure, a partial fixation structure that extends around less than 360° of the native valve anulus region, a low-profile fixation structure as illustrated in FIG. 4 below), and/or the coaptation member-clip configuration can be coupled to other types of tissue fixation structures (e.g., a sub-annular fixation structure). In further embodiments, the device 300 can be configured to be engaged with the three scallops of the anterior leaflet AL, and/or the device 300 can include clip mechanisms that engage opposing leaflets.

FIG. 4 is a side cross-sectional view of a valve repair device 400 ("device 400") implanted at a mitral valve in accordance with embodiments of the present technology. The device 400 can include various features at least generally similar to the features of the devices 100, 200, 300 described above with respect to FIGS. 1A-3B. For example, the device 400 includes a fixation member 402 for engaging at least a portion of the atrial wall, a frictional element 422 projecting from the fixation member 402, a coaptation member 404 depending from the fixation member 402 and configured to be positioned between the native leaflets (e.g., extending in front of the posterior leaflet PL), and a plurality of clip mechanisms 416 (identified individually as a first clip mechanism 416a and a second clip mechanism 416b) configured to extend behind and engage portions of the native leaflets. In the illustrated embodiment, the first clip mechanism 416a extends behind and engages the posterior leaflet PL, and the second clip mechanism 416b extends behind and engages a portion of the anterior leaflet AL such that the opposing native leaflets are both clipped. In these and other embodiments, the device 400 can include more than two clip mechanisms 416 positioned to engage different or additional portions of the native leaflets, and/or the two clip mechanisms 416 can be arranged to engage different portions of the same native leaflet.

The fixation member 404 can have features similar to the fixation members 102, 202 described above with respect to FIGS. 1A-2A (e.g., a mesh frame, cover, frictional element 422). However, the width of the portion of the fixation member 402 that extends around the atrium is narrower (in the direction of the flow axis) than that of the fixation members 102, 202, and therefore the outward-facing surface of the fixation member 402 engages with less atrial tissue. Still, with the sub-annular fixation provided by the multiple clip mechanisms 416, the low-profile fixation member 404 is expected to help avoid or prevent migration of the coaptation member 404 and provide a platform for tissue ingrowth. Further, given its smaller size, the low-profile fixation member 404 can be crimped or otherwise compressed to a smaller cross-sectional dimension within a delivery catheter (not shown) to facilitate intravascular delivery.

As shown in FIG. 4, in some embodiments the low-profile fixation member 402 can include one or more connection elements 424 (identified individually as a first connection element 424a and a second connection element 424b) that join the fixation member 402 to the coaptation member 404 and/or the clip mechanisms 416. For example, the connection elements 424 can extend in a downstream direction from the fixation member 402 to connect with a medial or central portion of the coaptation member 404, nearer to the inner portion of the coaptation member 404 than the outer portion. That is, the connection elements 424 can connect to portions of the coaptation member 404 positioned toward a central location within the valve in comparison with the outer, posterior-only connection described above with respect to FIGS. 1A-3B. In some embodiments, the connection elements 424 are used in place of the outer side connection, whereas in further embodiments the device 400 can include both the outer side connection and the inner/central connection elements 424. In various embodiments, the connection elements 426 can extend into the body of the coaptation member 404 (e.g., via slits in the cover) and connect with structures therein (e.g., as indicated by broken lines). In other embodiments, the device 400 can include additional fixation-coaptation connection elements 424 or the connection elements 424 may be omitted.

Figure 5A:
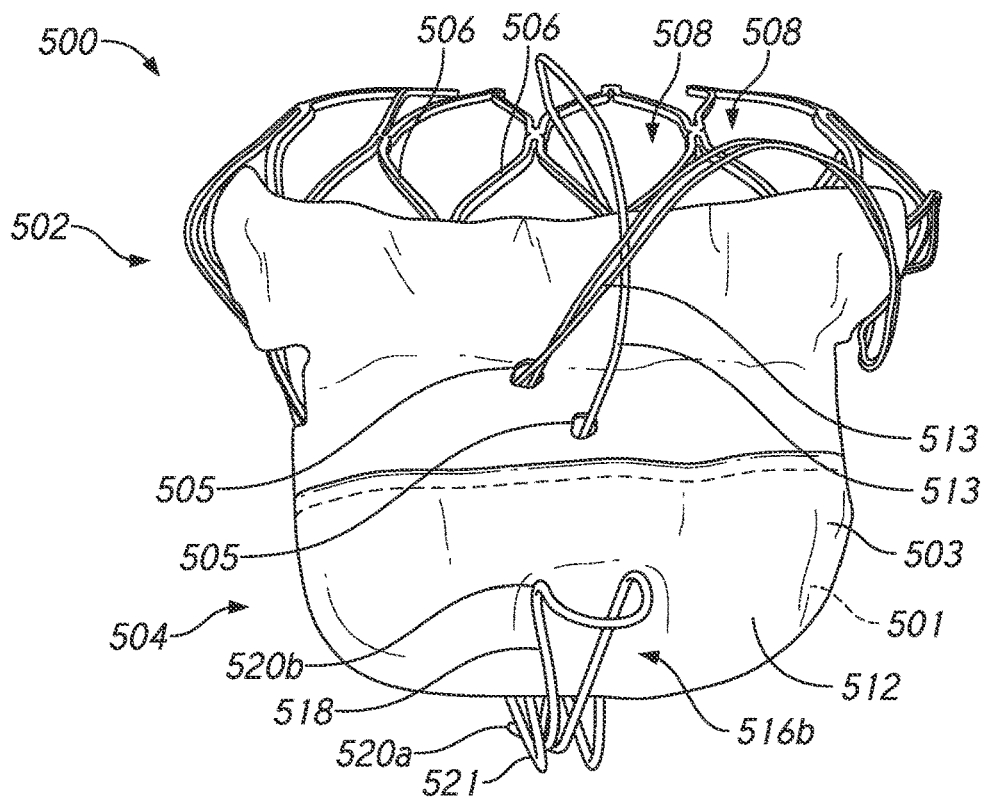
FIGS. 5A and 5B are front and side views of a valve repair device with a posterior fixation member configured in accordance with embodiments of the present technology.
Figure 5B:
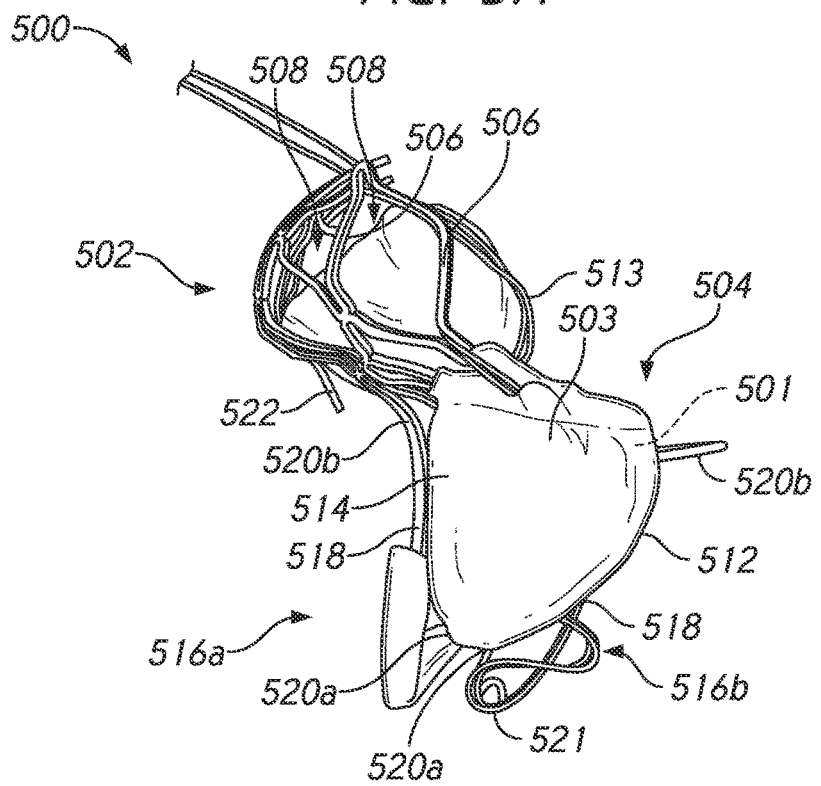

FIGS. 5A and 5B are front and side views of a valve repair device 500 ("device 500") configured in accordance with embodiments of the present technology. The device 500 includes various features at least generally similar to the features of the devices 100-400 described above with respect to FIGS. 1A-4. For example, the device 500 includes a fixation member 502 for engaging a portion of the atrial wall, frictional elements 522 projecting from the fixation member 502, a coaptation member 504 depending from the fixation member 502 and configured to be positioned between the native leaflets, and a plurality of clip mechanisms 516 (identified individually as a first clip mechanism 516a and a second clip mechanism 516b) configured to extend behind and engage portions of the native leaflets. Similar to the fixation members 102, 202 described above with respect to FIGS. 1A-2A, the fixation member 502 can include a plurality of struts 506 and open cells 508 that form a frame-like structure and an optional fabric cover on a portion of the struts 506. In the embodiment illustrated in FIGS. 5A and 5B, however, the fixation member 502 does not form a fully circumferential support, and instead provides an engagement structure that is configured to extend along non-circumferential section of the atrium. For example, the partial fixation member 502 can be configured to engage only a posterior portion of the atrial wall. The partial fixation member 502 (also referred to as a "posterior fixation member") can be crimped or otherwise reduced in profile to a smaller cross-sectional dimension to facilitate intravascular delivery. Further, in view of the stabilization provided by the multiple clip mechanisms, the partial fixation member 502 may provide sufficient atrial fixation to avoid ventricular migration.

As further shown in FIGS. 5A and 5B, the first clip mechanism 516a depends from an outer portion 514 of the coaptation member 504 such that it can capture and grasp a portion of a native leaflet displaced by the coaptation member 504 (e.g., the posterior leaflet), and the second clip mechanism 516b depends from an inner portion 512 of the coaptation member 504 such that it can capture and grasp a portion of an opposing native leaflet (e.g., the anterior leaflet). In some embodiments, the clip mechanisms 516 can be arranged to engage different portions of the same native leaflet, and/or the device 500 can include additional clip mechanisms 516 to grasp additional or different portions of the native leaflets. The clip mechanisms 516 can include features generally similar to the clip mechanisms 116-416 described above. For example, the clip mechanisms 516 each include a base portion 520a coupled to the coaptation member 504, a free end portion 520b extending therefrom, and an articulatable arm 518 that moves between an open and shut state via an actuation mechanism 521 (e.g., a spring-loaded lever). FIG. 5A further illustrates tensile members 513 (e.g., sutures) extending into the cavity of the coaptation member 504 via an opening 505 in a baffle cover 503, where the tensile members 513 operably couple to the actuation mechanisms 521 to enable clip actuation.

The coaptation member includes a frame 501 and a covering 503 similar to the coaptation members 104-404 described above. In some embodiments, the surface of the inner portion 512 of the coaptation member 504 (or a portion thereof) can initially function as a coaptation surface. For example, the lateral portions of the inner surface 512 may serve as a coaptation surface with the leaflet engaged at a central portion via the second clip mechanism 516b, or the entire inner surface 512 can serve as a coaptation surface (without the secondary clip mechanism 516b). At some time after deployment (e.g., during the same procedure or a time period thereafter), a section of the inner face 512 can be actuated to open up and capture a portion of the opposing native leaflet. When not in use, this actuating section (e.g., the anteriorly-facing portion of the second clip mechanism 516b) can be sized and shaped to lay substantially or completely flat against the surface of the inner portion or may be positioned within the coaptation member 506 adjacent to the inner surface. This interior and/or flush positioning of the actuating section avoids irritation of the opposing leaflet (e.g., the native leaflet) as it coapts against the baffle surface. In some embodiments, there may be more than one actuating section include more than one flush or internally positioned clip mechanism, so that the opposing leaflet (e.g., the anterior leaflet) can be attached to the baffle more medially or more laterally. By attaching to the opposing leaflet with more than one clip mechanism, the leaflet could be attached along an extended portion of the coaptation member 504.

Figure 6:
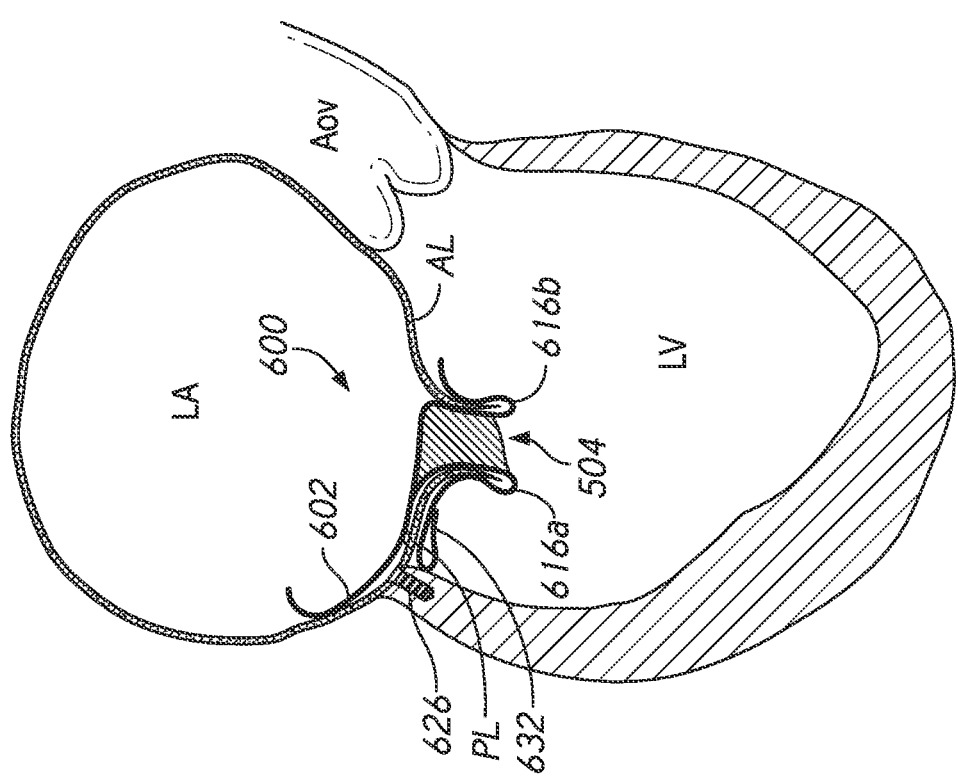
FIG. 6 is a side cross-sectional view of a valve repair device with a posterior fixation member implanted at a mitral valve in accordance with embodiments of the present technology.

FIG. 6 is a side cross-sectional view of a valve repair device 600 ("device 600") with a posterior fixation member implanted at a mitral valve in accordance with embodiments of the present technology. The device 600 can include various features at least generally similar to the features of the devices 100-500 described above with respect to FIGS. 1A-5B. For example, the device 600 includes a partial fixation member 602 for engaging at least a portion of the atrial wall, a coaptation member 604 depending from the fixation member 602 and configured to be positioned between the native leaflets, and a plurality of clip mechanisms 616 (identified individually as a first clip mechanism 616a and a second clip mechanism 616b) configured to extend behind and engage portions of the native leaflets. As shown in FIG. 6, the fixation member 602 may position the coaptation member 604 laterally outwardly in a central location within the valve orifice between the opposing valve leaflets, rather than angled to one side (e.g., posteriorly or anteriorly). The device 600 may further include a tissue anchoring feature 626 projecting from the fixation member 602 and configured to penetrate tissue to enhance fixation of the device 600. The tissue anchoring feature 626 can include a helical winding similar to a corkscrew shape, a screw-like structure, a hook, post, barb, and/or other features that enhance engagement via tissue penetration and/or frictional engagement. In some embodiments, the coaptation member 604 can be biased to one side and/or the device 600 can include additional or different tissue anchoring elements.

As further shown in FIG. 6, the primary clip mechanism 616a includes an extension along its articulatable arm that defines a sub-annular anchoring section 632 for enhanced sub-annular anchoring and stabilization. The sub-annular anchoring section 632 can be sized and shape to curve under the native annulus (e.g., an inverted U-shape) and press against or otherwise engage the adjacent sub-annular tissue. In some embodiments, the sub-annular anchoring section 632 extends a longer or shorter distance under the native annulus, curves back in a downstream direction along the adjacent tissue (e.g., along a septum or cardiac wall to form an inverted U-like shape), and/or otherwise engages with the surrounding cardiac tissue. In some embodiments, the sub-annular anchoring section 632 includes frictional elements (e.g., barbs, prongs, tines, corrugations) that enhance engagement and tissue ingrowth with the adjacent tissue. Further, in some embodiments, the clip mechanisms 616 can engage different portions of the native leaflets, and/or the device 600 may include additional clip mechanisms 616.

Figure 7:
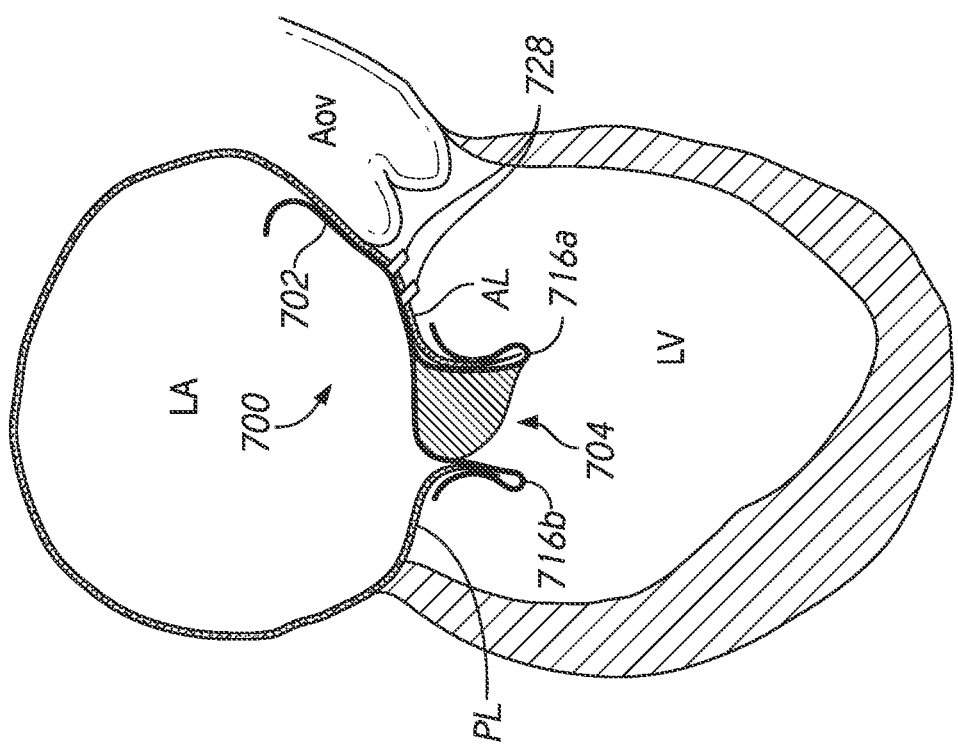
FIG. 7 is a side cross-sectional view of a valve repair device with an anterior fixation member implanted at a mitral valve in accordance with embodiments of the present technology.

FIG. 7 is a side cross-sectional view of a valve repair device 700 ("device 700") implanted at a mitral valve in accordance with embodiments of the present technology. The device 700 can include various features at least generally similar to the features of the devices 100-600 described above with respect to FIGS. 1A-6. For example, the device 700 includes a partial fixation member 702 for engaging a portion of the atrial wall, a coaptation member 704 depending from the fixation member 702 and configured to be positioned between the native leaflets, and a plurality of clip mechanisms 716 (identified individually as a first clip mechanism 716a and a second clip mechanism 716b) configured to extend behind and engage portions of the native leaflets. In the embodiment illustrated in FIG. 7, the partial fixation member 702 is configured to engage an anterior portion of the atrium, rather than the posterior portion. As such, the primary clip mechanism 716a at the outer portion of the coaptation member 704 engages the anterior leaflet AL and the secondary clip mechanism 716b engages the posterior leaflet PL. In various embodiments, the clip mechanisms 716 can engage different portions of the native leaflets, and/or the device 700 may include additional clip mechanisms 716. The device 700 can further include additional anchoring elements 728 projecting outwardly from the fixation member 702 and configured to penetrate adjacent tissue (e.g., near the annulus). The anchoring elements 728 can be posts, screws, helical windings, tines, barbs, anchors, and/or other features that serve to anchor and stabilize the device 700.

Figure 8:
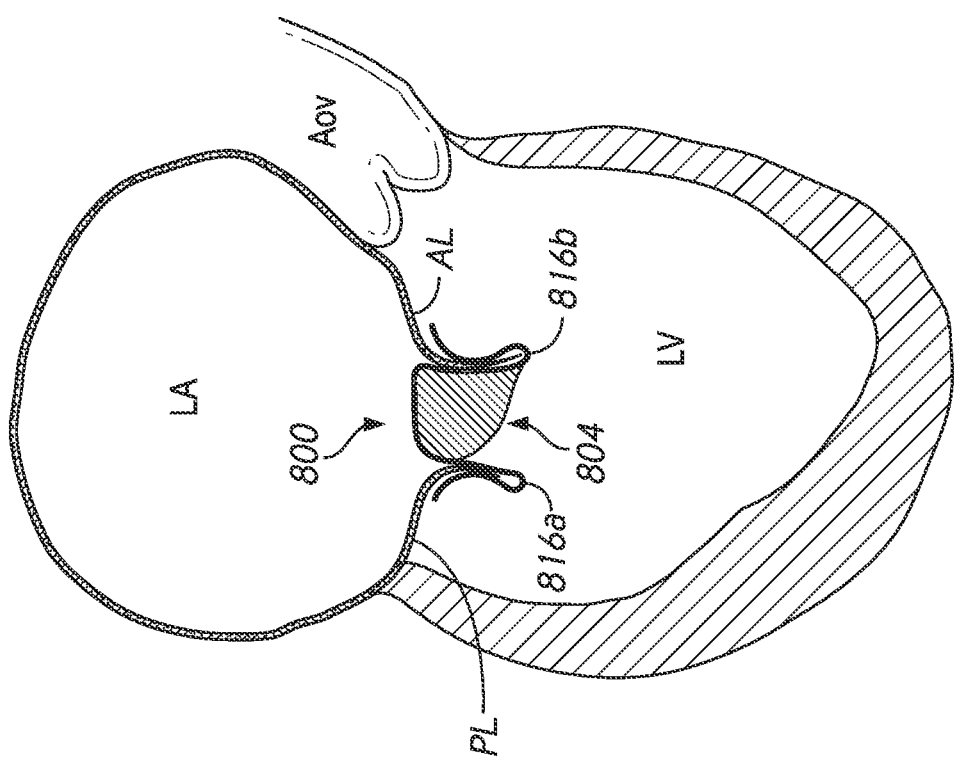
FIG. 8 is a side cross-sectional view of a valve repair device implanted at a mitral valve in accordance with embodiments of the present technology.

FIG. 8 is a side cross-sectional view of a valve repair device 800 ("device 800") implanted at a mitral valve in accordance with embodiments of the present technology. The device 800 can include various features at least generally similar to the features of the devices 100-700 described above with respect to FIGS. 1A-7. For example, the device 800 includes a coaptation member 804 configured to be positioned between the native leaflets and a plurality of clip mechanisms 816 (identified individually as a first clip mechanism 816a and a second clip mechanism 816b) configured to extend behind and engage portions of the native leaflets. The coaptation member 804 can be centrally located between the leaflets, the first clip mechanism 816a can extend behind and grasp the posterior leaflet PL, and the second clip mechanism 816b can extend behind and capture the opposing anterior leaflet AL. In the illustrated embodiment, the device 800 does not include an atrial or supra-annular fixation member. Instead, the combination of the space-filling coaptation member 804 and the clip mechanism 816 provide sufficient stabilization an anchoring within the valve.

In various embodiments, the coaptation member 804 can be adjustable to extend in length between the commissures of the leaflets (e.g., from the posterior commissure to the anterior commissure) and/or the depth with which it protrudes within the annulus. For example, the coaptation member 804 can include an expandable body within the cavity of the coaptation member 804 that expands to increase one or more dimensions of the device. The coaptation member 804 may also or alternatively include semi-rigid rods that are moved or inserted to initiate expansion and/or expandable appendages that increase the dimensions of the coaptation member 804. This adjustability can provide for appropriate anchoring within the valve and proper coaptation of the leaflets against the coaptation member 804 and/or each other in view of the patient's anatomy. In some embodiments, the clip mechanisms 816 can engage different portions of the native leaflets, and/or the device 800 may include additional clip mechanisms 816 for engaging other portions of the native leaflets. In some embodiments, the device 800 can include additional sub-annular fixation mechanisms, such as anchoring components, frictional elements, and/or extensions of the clip arm.

FIGS. 9A and 9B are side cross-sectional views of a valve repair device 900 ("device 900") positioned in a mitral valve during an intermediate delivery stage and an implanted stage, respectively, in accordance with embodiments of the present technology. The device 900 can include various features similar to the features of the devices 100, 200, 300, 400, 500, 600, 700 described above with respect to FIGS. 1A-7. For example, the device 900 includes a fixation member 902 for engaging at least a portion of the atrial wall, an anchoring element 926 that penetrates tissue proximate to the native annulus, a coaptation member 904 depending from the fixation member 902 and configured to be positioned between the native leaflets (e.g., extending in front of the posterior leaflet PL), and a plurality of clipping mechanisms 916 (identified individually as a first clip mechanism 916a and a second clip mechanism 916b) configured to extend behind and engage portions of the native leaflets. In the illustrated embodiment, the fixation member 902 is a partial fixation member (e.g., similar to those described above with respect to FIGS. 5 and 6) that engages a non-circumferential portion (e.g., a posterior portion) of the atrial wall, and the coaptation member 904 depends from the fixation member 902 in a manner that positions the coaptation member 904 in a central location within the annulus, rather than angled to one side. In various embodiments, the fixation member 902 can be sized and shaped to extend along and engage a different section of the atrium (e.g., an anterior section), may extend around a circumferential portion of the atrium or annulus, have a low profile along the flow axis, or may be omitted. In some embodiments, the device 900 can include additional or different anchoring elements 926 or the anchoring element 926 may be omitted. In some embodiments, the coaptation member 904 is positioned to one side of the native annulus toward one of the native leaflets (e.g., angled posteriorly or anteriorly).

As show in the embodiment illustrated in FIGS. 9A and 9B, the first clipping mechanism 916a projects from an outwardly-facing surface of the coaptation member 904 to engage a portion of the posterior leaflet PL, whereas the second clipping mechanism 916b is a separate component independently movable with respect to the coaptation member-primary clip structure and configured to engage a native leaflet (e.g., the anterior leaflet AL) opposing the coaptation member 904. In this embodiment, the coaptation member 904 further includes a clip engagement element 930a (also referred to as a "locking element" or "locking feature") along, within, or accessible via the coaptation surface of the coaptation member 904. The clip engagement element 930a can interact with a complimentary engagement feature 930b of the independent secondary clip mechanism 916b (e.g., on an inward-facing section or face on the base portion 920a of the clip mechanism 916b) and/or with a portion of the independent secondary clip mechanism 916b itself to affix the two components together.

The first and second engagement elements 930a and 930b (collectively referred to as "engagement elements 930") may include one or more fastening means for drawing the coaptation member 904 and the independent clipping mechanism 916b toward each other and maintaining the connection therebetween. For example, each engagement element 930 may include one or more magnetic members positioned along the inward-facing surfaces of the coaptation member 904 and the independent secondary clipping mechanism 916b, with each component's magnetic member(s) having an opposite pole. In this embodiment, the second clip mechanism 916b can be first clipped to a portion of the leaflet (e.g., the anterior leaflet AL as shown in FIG. 9A) opposing the coaptation member 904, and then the magnetic engagement elements 930 can draw the secondary clipping mechanism 916b toward the coaptation member 904 (e.g., facilitated during systole) and maintain the connection to each other via the magnetic force therebetween. In some embodiments, the engagement elements 930 are mechanical features, such as a pin-in-slot mechanism, threaded components, rivet components, interlocking surfaces, hooks, and/or staples, that lock or actuate the independent secondary clipping mechanism 916b to or through the coaptation member 904. In some embodiments, the engagement elements 930 include adhesives, sutures, external fasteners, and/or other suitable components for joining and maintaining a connection between the coaptation member 904 and the independent clip mechanism 916b. In some embodiments, only one of the coaptation member 904 or the independent clip mechanism 916b includes the engagement element 930 for securing the two components together.

In some embodiments, the device 900 includes multiple features that aid to join and lock the coaptation member 904 to the independent secondary clip mechanism 916b. For example, in various embodiments the engagement elements 930 include magnetic features that serve to draw the coaptation member 904 and the independent clipping mechanism 916b together and provide initial engagement of the two components. After the coaptation member 904 and the independent clip mechanism 916b are brought in proximity with each other and, in some embodiments, temporarily joined together, the initial connection is replaced by (or supplemented with) a non-magnetic engagement feature (e.g., a mechanical connection) for a more permanent, MRI-compatible attachment. In various embodiments, the device 900 can use different features for initial attachment and more permanent connection.

During device delivery, the main device component (including the optional fixation member 902, the coaptation member 904, and the primary clip mechanism 916a) can be implanted at the native valve as described above. For example, as shown in FIG. 9A the main device component can be delivered intravascularly (e.g., via a trans-aortic or trans-atrial delivery) at the mitral valve, and the primary clip mechanism 916a can be actuated to extend behind and engage a portion (e.g., P2) the posterior leaflet PL. The main device component may also include one or more additional clip mechanisms (not shown) for engaging different portions of the posterior leaflet PL (e.g., P1 and/or P2). In some embodiments, the coaptation member 904 can function as a new coaptation surface for the anterior leaflet AL without further intervention for a period of time.

The independent secondary clip mechanism 916b can be delivered intravascularly (e.g., via a trans-aortic or trans-atrial delivery) either during the same procedure as the main component implant, or in a subsequent procedure at a later time. For example, the secondary clip mechanism 916b can be implanted after a period of (e.g., days, months, or potentially years) after initial implant of the main device component to allow the clinician to assess the fixation and function of the native valve (e.g., coaptation without the secondary clip mechanism and accommodate changing anatomy of the patient over time. When the secondary opposing clip mechanism 916b is implanted (either in the same or a subsequent procedure), the clinician can actuate the independent secondary clip mechanism 916b such that it sandwiches a portion of the free native leaflet (e.g., the anterior leaflet AL) between the base portion 920a and the free portion 920b and secures itself to the native leaflet. The actuation and structure of the independent secondary clip mechanism 916b may be similar to the actuation mechanisms and structures of the permanently attached clip mechanisms described above. For example, the independent clip mechanism 916b may include a spring-loaded arm member 918 that can be actuated to move between an open state and a closed state by pulling a suture or other tensile member that extends through the delivery catheter. When the independent clip mechanism 916b is delivered in the same procedure as the coaptation member 904, the independent clip mechanism 916b can be housed in the same delivery catheter as the coaptation member 904 and deployed sequentially before or after the coaptation member 904. In some embodiments, the independent clip mechanism 916b may be deployed from a separate catheter.

After the independent clip mechanism 916b is affixed to the corresponding native leaflet (e.g., the anterior leaflet AL), the independent clip mechanism 916b can be drawn toward the coaptation member 904 such that the inwardly-facing surface of the independent clip mechanism 916b (e.g., the surface of the base portion 920a facing toward the native annulus) is in line with a portion of the coaptation surface of the coaptation member 904, and the two components can be joined together via the one or more engagement elements 930. In some embodiments, the delivery system can be coupled to the deployed independent clip mechanism 916b (e.g., via tensile members, the catheter itself, springs) and used to draw the independent clip mechanism 916b in an upstream and/or transverse direction toward the coaptation member 904 (e.g., via proximal movement of the tensile member, catheter, or spring). In some embodiments, the two components are drawn together via the engagement elements 930 themselves, such as the magnetic features described above, a suture loop engagement, and/or other joining mechanism. In some embodiments, the natural motion of the native leaflets during systole facilitates driving the components together. Once drawn into appropriate proximity to and alignment with each other, the independent clip mechanism 916b and the coaptation member 904 can be affixed together via the engagement elements 930, which may be the same as the means used to position the two components together and/or different locking mechanisms. Once the independent secondary clip mechanism 916b is affixed to the coaptation member 904, the device 900 can function in a similar manner as the devices described above with integrated secondary clip mechanism 916b. In some embodiments, the device 900 may include more than one independent clip mechanism such that the two or more independent clip mechanisms are configured to engage different portions of the native leaflet opposing the coaptation member 904 (e.g., A1, A2, and/or A3 of the anterior leaflet AL). In these and other embodiments, the device 900 can include one or more intendent clip mechanisms that are configured to engage different portions of the native leaflet to which the primary clip mechanism 916a is attached.

In various embodiments, the body of the coaptation member 904, having an internal open volume, can be sized and shaped to house the independent clip mechanism 916b and/or multiple independent clip mechanisms. The independent clip mechanism 916b can be initially retracted within the coaptation member 904 and the delivery system. After deploying the coaptation member 904, the independent clip mechanism 916b can then be optionally deployed by pushing it pushed outwardly in a downstream, linear direction from an inferior end portion of the coaptation member 904 (e.g., via an opening or slit in the downstream end of the coaptation member 904. As the independent clip mechanism 916b is advanced out of the coaptation member 904, it initially extends distally from the coaptation member 904 in an inverted orientation with the curved/U-shape open to the apical region of the heart and the base portion 920a positioned closer to the opposing native leaflet. Once the curved/U-shaped portion of the independent clip mechanism 916b is advanced out of the body of the coaptation member 904, the independent clip mechanism 916b reverts to its properly-oriented curved/U-shape and the independent clip mechanism 916b flips up under the anterior leaflet AL, grasping it and trapping it against the coaptation surface of the coaptation member 904. In other embodiments, the independent clip mechanism 916b may be deployed differently from its position housed in the coaptation member 904. Because the coaptation member 904 extends further towards the opposing anterior leaflet AL than other types of clip devices that do not include a structured body, the independent clip mechanism 916b does not need to have secondary graspers or apply significant force to hold the anterior leaflet AL against the independent clip mechanism 916b.

In these embodiments with independent clip mechanisms, the independent clip mechanism 916b can be an optional element of the implant procedure. For example, the coaptation member 904 can first be delivered and attached to the posterior leaflet PL. If regurgitation persists and it is likely that clipping another leaflet to the coaptation member 904 will address that persistent regurgitation, then the independent clip mechanism 916b can be actuated or otherwise delivered.

Figure 10:
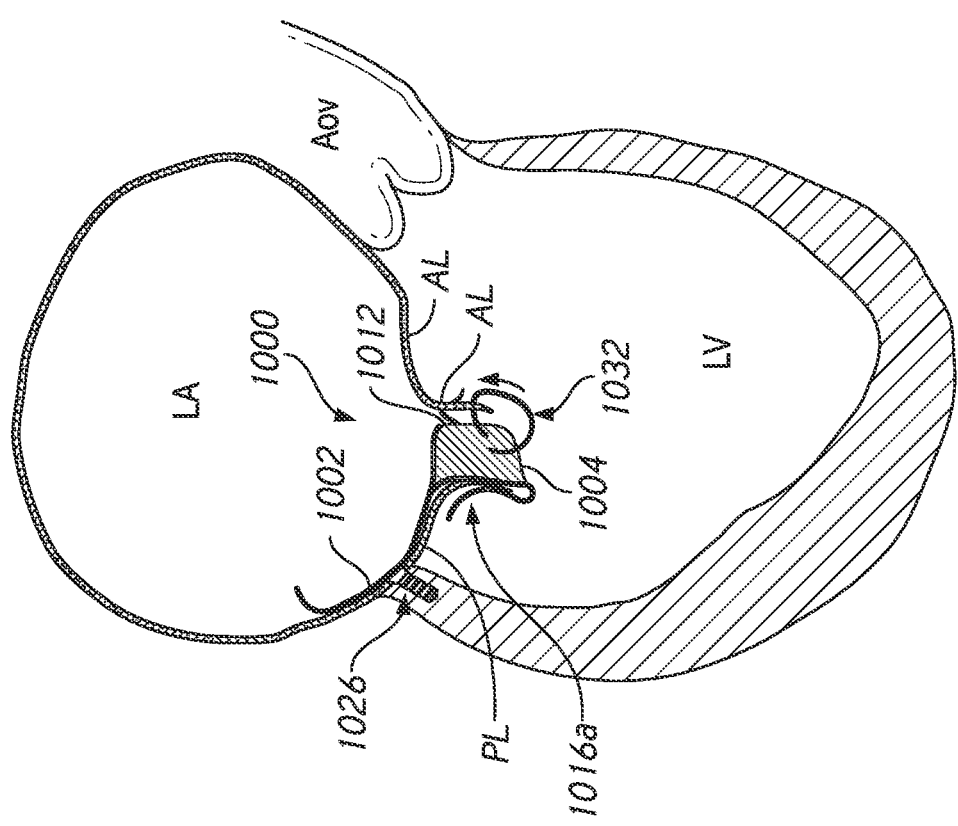
FIG. 10 is a side cross-sectional view of a valve repair device implanted at a mitral valve in accordance with embodiments of the present technology.

FIG. 10 is a side cross-sectional view of a valve repair device 1000 ("device 1000") positioned in a mitral valve in accordance with embodiments of the present technology. The device 1000 can include various features similar to the features of the devices 100-900 described above with respect to FIGS. 1A-9B. For example, the device 1000 includes a partial fixation member 1002 for engaging a section of the atrial wall (e.g., a posterior section), an anchoring element 1026 that penetrates tissue proximate to the native annulus, a coaptation member 1004 depending from the fixation member 1002 and configured to be positioned between the native leaflets (e.g., extending in front of the posterior leaflet PL), and a primary clipping mechanisms 1016 configured to extend behind and engage a portion of the native leaflet at the outer side 1014 of the coaptation member 1004. In various embodiments, the fixation member 1002 can be sized and shaped to extend along and engage a tissue along a different section of the atrium (e.g., an anterior section), may extend around a circumferential portion of the atrium or annulus, have a low profile along the flow axis, or may be omitted. In some embodiments, the device 1000 can include additional or different anchoring elements 1026 or the anchoring element 1026 may be omitted. In some embodiments, the coaptation member 1004 is positioned posteriorly to replace all or a portion of the posterior leaflet PL, positioned anteriorly to replace at least a portion of the anterior leaflet AL, and/or positioned in between the leaflets in a generally central location within the annulus.

As shown in FIG. 10, the device 1000 can further include an anterior leaflet capture element 1032 housed within the body of the coaptation member 1004 and configured to deploy therefrom to capture a portion (e.g., a ventricular edge portion) of the anterior leaflet AL, affixing it to coaptation member 1004. For example, the leaflet capture element 1032 may be a preferentially curved (e.g., U-shaped, J-shaped, C-shaped) hypotube and/or needle operably coupled to a delivery system handle (not shown). After the coaptation member 1004 has been implanted, manipulation of the delivery system handle can cause a leading end 1034 of the curved capture element 1032 to project outward from the distal end or inner side 1012 of the coaptation member 1004, move along the transverse axis to curve around the back side of the anterior leaflet AL, pierce through the anterior leaflet AL via a needle extending through the hypotube or a sharp portion of the leading end 1034, and extend back into the coaptation member 1004. As shown in FIG. 10, this causes the capture element 1032 to form a loop around the ventricular edge of anterior leaflet AL, with the capture element 1032 impaling the anterior leaflet AL, and allows the capture element 1032 to pull the anterior leaflet AL toward the inner side 112 against the coaptation surface or partially into the body of the coaptation member 1004 as the capture element 1032 is retracted into the coaptation member 1004. In various embodiments, the capture element 1032 (e.g., when the needle is omitted) does not pierce completely through native leaflet, and instead presses against the back side of the native leaflet to push it toward or into the coaptation member 1004. Accordingly, the device 1000 with the primary clip mechanism 1016*a* and the curved capture element 1032 can grasp the ends of opposing leaflets (e.g., the posterior leaflet PL and the anterior leaflet AL) to provide a similar edge-edge effect as a device with opposing clip mechanisms. In some embodiments, the device 1000 can include additional leaflet capture elements configured to capture different portions of the anterior leaflet AL and/or the posterior leaflet PL. In various embodiments, the device 1000 can further include one or more additional clip mechanisms configured to capture other portions of the anterior leaflet AL and/or the posterior leaflet PL.

FURTHER EXAMPLES

The following examples are illustrative of several embodiments of the present technology:
1. A valve repair device, comprising:
   an atrial fixation member configured to press against cardiac tissue proximate to a native valve annulus;
   a coaptation member extending away from the atrial fixation member and radially inward from the atrial fixation member, the coaptation member comprising an inner portion having a coaptation surface configured to coapt with a first native leaflet during systole, an outer portion configured to displace at least a portion of a second native leaflet, and a downstream end portion, wherein the coaptation member is substantially stationary during cardiac cycles; and
   a plurality of clip mechanisms depending from to the coaptation member, wherein each clip mechanism comprises a base portion coupled to the downstream end portion of the coaptation member, a free end portion unaffixed to the coaptation member, and an articulatable arm member extending in an upstream direction from the base portion and forming the free end portion, wherein the articulatable arm member is configured to capture a portion of either the first native leaflet or the second native leaflet between the articulatable arm member and the coaptation member.
2. The valve repair device of example 1 wherein the plurality of clip mechanisms comprises:
   a first clip mechanism extending from the outer portion of the coaptation member and configured to capture a portion of the second native leaflet; and
   a second clip mechanism extending from the inner portion of the coaptation member and configured to capture a portion of the first native leaflet.
3. The valve repair device of example 1 or 2 wherein the plurality of clip mechanisms comprises:
   a first clip mechanism extending from the outer portion of the coaptation member and configured to capture a central portion of the second native leaflet; and
   a second clip mechanism extending from the outer portion of the coaptation member and configured to capture a lateral portion of the second native leaflet.
4. The valve repair device of any one of the proceeding examples wherein the plurality of clip mechanisms comprises:
   a first clip mechanism extending from the outer portion of the coaptation member and configured to capture a central portion of the second native leaflet;
   a second clip mechanism extending from the outer portion of the coaptation member and configured to capture a first lateral portion of the second native leaflet; and
   a third clip mechanism extending from the outer portion of the coaptation member and configured to capture a second lateral portion of the second native leaflet.
5. The valve repair device of any one of the proceeding examples wherein the coaptation member is configured to be positioned in a mitral valve, the first native leaflet is an anterior leaflet, and the second native leaflet is a posterior leaflet, wherein the plurality of clip mechanisms comprises:
   a first clip mechanism extending from the outer portion of the coaptation member and configured to capture a P2 portion of the posterior leaflet;
   a second clip mechanism extending from the outer portion of the coaptation member and configured to capture a P3 portion of the anterior native leaflet; and
   a third clip mechanism extending from the outer portion of the coaptation member and configured to capture a P1 portion of the anterior native leaflet.
6. The valve repair device of any one of the proceeding examples wherein the coaptation member is configured to be positioned in a mitral valve, the first native leaflet is an anterior leaflet, and the second native leaflet is a posterior leaflet, wherein the plurality of clip mechanisms comprises:

a first clip mechanism extending from the outer portion of the coaptation member and configured to capture a central portion of the posterior leaflet; and a second clip mechanism extending from the inner portion of the coaptation member and configured to capture a central portion of the anterior native leaflet.
7. The valve repair device of any one of the proceeding examples wherein the fixation member is configured to position the coaptation member in a laterally offset from a valve orifice and angled toward the second valve leaflet.
8. The valve repair device of any one of the proceeding examples wherein the fixation member is configured to position the coaptation member in a central location within a valve orifice.
9. The valve repair device of any one of the proceeding examples wherein the fixation member comprises a plurality of interconnected struts that define rows of open cells, and wherein the fixation member is configured to engage cardiac tissue along a circumferential portion of a cardiac chamber.
10. The valve repair device any one of the proceeding examples wherein the fixation member comprises a plurality of interconnected struts that define rows of open cells, and wherein the fixation member is configured to engage cardiac tissue along a non-circumferential portion of a cardiac chamber.
11. The valve repair device of any one of the proceeding examples wherein the fixation member forms a low-profile frame structure configured to contact a circumferential portion of a cardiac chamber, and wherein the low-profile frame structure includes a connection element affixed to the inner portion of the coaptation member.
12. The valve repair device of any one of the proceeding examples wherein the coaptation member has a crescent shape along a transverse cross-section of the valve annulus.
13. The valve repair device of any one of the proceeding examples wherein the coaptation member extends along a length defined by opposing commissures of the first and second native leaflets.
14. The valve repair device of any one of the proceeding examples wherein the fixation member comprises a tissue anchor protruding from an inferior portion of the fixation member and configured to penetrate proximate to the native valve annulus.
15. The valve repair device of any one of the proceeding examples wherein the coaptation member comprises a stent structure configured to be increased in length between opposing commissures of the first and second native leaflets.
16. The valve repair device of any one of the proceeding examples wherein the coaptation member is configured to adjust in dimension across a cross-sectional length.
17. The valve repair device of example 16 wherein the coaptation member comprises expandable components to increase in width relative to a commissure line and/or protrusion depth into the native valve orifice.
18. The valve repair device of example 16 wherein the coaptation member is configured to receive rods that expand the coaptation member in width relative to a commissure line and/or protrusion depth into the native valve orifice.
19. The valve repair device of any one of the proceeding examples wherein:
the coaptation member comprises a first locking feature at the inner portion; and
the plurality of clip mechanisms comprises—
a first clip mechanism extending from the outer portion of the coaptation member and configured to capture a portion of the second native leaflet; and
an independent second clip mechanism having a second locking feature configured to engage with the first locking feature to affix the independent second clip mechanism to the inner portion of the coaptation member.
20. The valve repair device of example 19 wherein the independent second clip mechanism is configured to be housed within the coaptation member before deployment.
21. The valve repair device of example 19 wherein the first and second locking mechanisms comprise magnetic components.
22. The valve repair device of any one of the proceeding examples wherein the coaptation surface comprises actuation sections configured to open to capture portions of the first native leaflet.
23. The valve repair device of any one of the proceeding examples, further comprising a leaflet capture component housed in and deployable from the coaptation member and configured to pierce and capture the first native leaflet.
24. The valve repair device of any one of the proceeding examples wherein each of the clip mechanisms include a spring-loaded lever configured to move the articulatable arm between an open state and a closed state.
25. The valve repair device of any one of the proceeding examples wherein the articulatable arm of one of the clip mechanisms comprises a sub-annular engagement component extending from the free end portion and configured to engage sub-annular cardiac tissue.
26. A valve repair device, comprising:
a coaptation member configured to be positioned between a posterior leaflet and an anterior leaflet of a mitral valve, the coaptation member comprising—
a frame structure comprising a plurality of struts;
a cover extending along at least a portion of the frame structure and configured to form an enclosed chamber within the frame structure;
an anterior portion having a surface configured to displace or coapt with the anterior leaflet during systole; and
a posterior portion configured to displace or coapt with at least a portion of the posterior leaflet,
wherein the coaptation member is substantially stationary during cardiac cycles;
a plurality of clip mechanisms depending from the coaptation member, wherein one or more of clip mechanisms comprises—
a base portion coupled to the coaptation member,
an articulatable arm member extending in an upstream direction from the base portion and having a free end portion unaffixed to the coaptation member, wherein the articulatable arm member is configured to capture a portion of the posterior leaflet or the anterior leaflet between the articulatable arm member and coaptation member.
27. The valve repair device of example 26 wherein the plurality of clip mechanisms comprises:
a posterior clip mechanism extending from the posterior portion of the coaptation member and configured to capture a portion of the posterior leaflet; and an anterior clip mechanism extending from the anterior portion of the coaptation member and configured to capture a portion of the anterior leaflet.

28. The valve repair device of example 26 or 27 wherein the plurality of clip mechanisms comprises:
a primary posterior clip mechanism extending from the posterior portion of the coaptation member and configured to capture a central portion of the posterior leaflet; and
a secondary posterior clip mechanism extending from the posterior portion of the coaptation member and configured to capture a lateral portion of the posterior leaflet.

29. The valve repair device of example 28 wherein the lateral portion is a first lateral portion, and wherein the plurality of clip mechanisms further comprises:
a tertiary clip mechanism extending from the posterior portion of the coaptation member and configured to capture a second lateral portion of the posterior leaflet.

30. The valve repair device of any one of the proceeding examples, further comprising an atrial fixation member coupled to the coaptation member and configured to engage cardiac tissue within a left atrium, wherein the coaptation member extends radially inward from the atrial fixation member.

31. The valve repair device of example 30 wherein the fixation member comprises a frame structure configured to engage cardiac tissue along a circumferential portion of the left atrium.

32. The valve repair device example 30 wherein the fixation member comprises a frame structure configured to engage cardiac tissue along a non-circumferential, posterior portion of the left atrium.

33. The valve repair device example 30 wherein the fixation member comprises a frame structure configured to engage cardiac tissue along a non-circumferential, anterior portion of the left atrium.

34. The valve repair device of example 30 wherein the coaptation member has a width configured to extend at least across a central scallop of the posterior leaflet.

35. The valve repair device of any one of the proceeding examples wherein the coaptation member is configured to include an expandable structure for adjusting a width of the coaptation member relative to a commissure line and/or protrusion depth into the native mitral valve orifice.

36. The valve repair device of any one of the proceeding examples wherein:
the coaptation member comprises a first locking feature at the anterior portion; and
the plurality of clip mechanisms comprises—
a posterior clip mechanism extending from the posterior portion of the coaptation member and configured to capture a portion of the posterior leaflet; and
an independent anterior clip mechanism having a second locking feature configured to engage with the first locking feature to affix the independent second clip mechanism to the inner portion of the coaptation member, wherein the anterior clip mechanism is configured to engage the anterior leaflet.

37. The valve repair device of any one of the proceeding examples wherein the plurality of clip mechanisms comprises:
a posterior clip mechanism extending from the posterior portion of the coaptation member and configured to capture a portion of the posterior leaflet; and
an independent anterior clip mechanism configured to be housed within the coaptation member and engage the anterior leaflet.

38. The valve repair device of any one of the proceeding examples, further comprising a leaflet capture component housed in and deployable from the coaptation member and configured to pierce and capture the anterior leaflet.

39. The valve repair device of any one of the proceeding examples wherein each of the clip mechanisms include a spring-loaded lever configured to move the articulatable arm between an open state and a closed state.

40. The valve repair device of any one of the proceeding examples wherein the articulatable arm of one of the clip mechanisms comprises a sub-annular engagement component configured to engage sub-annular cardiac tissue.

41. A method repairing a cardiac valve, the method comprising:
deploying a coaptation member of a valve repair device in a regurgitant valve orifice between a first native leaflet and a second native leaflet, wherein the coaptation has a first portion facing the first native leaflet and a second portion facing the second native leaflet, the coaptation member defining an open cavity that spaces the first and second portions apart from each other;
extending a first articulatable arm of a first clip mechanism behind a central portion the first native leaflet such that the central portion of the first native leaflet is positioned between the first articulatable arm and the first portion of the coaptation member;
actuating the first articulatable arm to move to a closed state in which the first articulatable arm presses the first native leaflet between the first articulatable arm and the first portion;
extending a second articulatable arm of a second clip mechanism behind either a lateral portion of the first native leaflet or a central portion of the second native leaflet; and
actuating the second articulatable arm to move to a closed state in which the second articulatable arm clamps to the leaflet portion.

42. The method of example 41, further comprising deploying a fixation member of the valve repair device against an atrial wall such that the fixation member encircles a native valve annulus, the fixation member forming a central lumen through which blood flows.

43. The method of example 41 or 42, further comprising deploying a partial fixation member of the valve repair device to engage tissue against a section of an atrial wall.

44. The method of any one of the proceeding examples wherein:
extending the second articulatable arm of the second clip mechanism comprises extending the second articulatable arm behind a lateral portion of the first native leaflet; and
actuating the second articulatable arm comprises engaging the lateral portion of the first native leaflet between the second articulatable arm and the first portion.

45. The method of example 44 wherein the lateral portion is a first lateral portion, and wherein:
extending a third articulatable arm of a third clip mechanism behind a second lateral portion of the first native leaflet; and actuating the third articulatable arm to engage the second lateral portion of the first native leaflet between the third articulatable arm and the first portion.

46. The method of any one of the proceeding examples wherein:

extending the second articulatable arm of the second clip mechanism comprises extending the second articulatable arm behind a central portion of the second native leaflet; and actuating the second articulatable arm comprises engaging the second native leaflet between the second articulatable arm and the second portion.

47. The method of any one of the proceeding examples wherein deploying the coaptation member extending the coaptation member across at least a central scallop of the first native leaflet.

48. The method of any one of the proceeding examples, further comprising adjusting a width of the coaptation member across the native valve annulus.

49. The method of any one of the proceeding examples, further comprising increasing a dimension of the coaptation member beyond a natural expansion of the coaptation member.

50. The method of any one of the proceeding examples, further comprising deploying the second clip mechanism from within the cavity of the coaptation member.

51. The method of example 50, further comprising locking a base portion of the second clip mechanism to a second portion of the coaptation member.

52. The method of any one of the proceeding examples, further comprising:

deploying a leaflet capture component from the coaptation member; and piercing through the second native leaflet to pull the second native leaflet against the coaptation member.

53. The method of any one of the proceeding examples, further comprising engaging sub-annular cardiac tissue with a sub-annular engagement component extending from the first clip mechanism.

54. The method of any one of the proceeding examples wherein deploying the coaptation member of the valve repair device in the regurgitant valve orifice between the first native leaflet and the second native leaflet comprises deploying the coaptation member of the valve repair device in a mitral valve orifice between a posterior leaflet and an anterior leaflet.

CONCLUSION

The above detailed description of embodiments of the technology are not intended to be exhaustive or to limit the technology to the precise form disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments can perform steps in a different order. The various embodiments described herein can also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms can also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications can be made without deviating from the technology. Further, while advantages associated with some embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

We claim:

1. A valve repair device, comprising:

an atrial fixation member configured to press against cardiac tissue proximate to a native valve annulus;

a coaptation member extending away from the atrial fixation member and radially inward from the atrial fixation member, the coaptation member comprising an inner portion having a coaptation surface configured to coapt with a first native leaflet during systole, an outer portion configured to displace at least a portion of a second native leaflet, and a downstream end portion, wherein the coaptation member is substantially stationary during cardiac cycles, and wherein the coaptation member defines an interior volume and an opening to the interior volume; and a plurality of clip mechanisms depending from the coaptation member, wherein each clip mechanism comprises— a base portion coupled to the downstream end portion of the coaptation member, a free end portion unaffixed to the coaptation member, an articulatable arm member extending in an upstream direction from the base portion and forming the free end portion, wherein the articulatable arm member is configured to capture a portion of either the first native leaflet or the second native leaflet between the articulatable arm member and the coaptation member, and an actuation mechanism configured to move the articulatable arm member between a closed position and an open position;

wherein each of the actuation mechanisms is independently actuatable via a delivery component inserted through the opening in the coaptation member and into the interior volume of the coaptation member.

2. The valve repair device of claim 1 wherein the plurality of clip mechanisms comprises:

a first clip mechanism extending from the outer portion of the coaptation member and configured to capture a portion of the second native leaflet; and a second clip mechanism extending from the inner portion of the coaptation member and configured to capture a portion of the first native leaflet.

3. The valve repair device of claim 1 wherein the plurality of clip mechanisms comprises:
   a first clip mechanism extending from the outer portion of the coaptation member and configured to capture a central portion of the second native leaflet; and
   a second clip mechanism extending from the outer portion of the coaptation member and configured to capture a lateral portion of the second native leaflet.

4. The valve repair device of claim 1 wherein the plurality of clip mechanisms comprises:
   a first clip mechanism extending from the outer portion of the coaptation member and configured to capture a central portion of the second native leaflet;
   a second clip mechanism extending from the outer portion of the coaptation member and configured to capture a first lateral portion of the second native leaflet; and
   a third clip mechanism extending from the outer portion of the coaptation member and configured to capture a second lateral portion of the second native leaflet.

5. The valve repair device of claim 1 wherein the coaptation member is configured to be positioned in a mitral valve, the first native leaflet is an anterior leaflet, and the second native leaflet is a posterior leaflet, wherein the plurality of clip mechanisms comprises:
   a first clip mechanism extending from the outer portion of the coaptation member and configured to capture a P2 portion of the posterior leaflet;
   a second clip mechanism extending from the outer portion of the coaptation member and configured to capture a P3 portion of the anterior native leaflet; and
   a third clip mechanism extending from the outer portion of the coaptation member and configured to capture a P1 portion of the anterior native leaflet.

6. The valve repair device of claim 1 wherein the coaptation member is configured to be positioned in a mitral valve, the first native leaflet is an anterior leaflet, and the second native leaflet is a posterior leaflet, wherein the plurality of clip mechanisms comprises:
   a first clip mechanism extending from the outer portion of the coaptation member and configured to capture a central portion of the posterior leaflet; and
   a second clip mechanism extending from the inner portion of the coaptation member and configured to capture a central portion of the anterior native leaflet.

7. The valve repair device of claim 1 wherein the fixation member is configured to position the coaptation member in a laterally offset from a valve orifice and angled toward the second valve leaflet.

8. The valve repair device of claim 1 wherein the fixation member is configured to position the coaptation member in a central location within a valve orifice.

9. The valve repair device of claim 1 wherein the fixation member comprises a plurality of interconnected struts that define rows of open cells, and wherein the fixation member is configured to engage cardiac tissue along a circumferential portion of a cardiac chamber.

10. The valve repair device claim 1 wherein the fixation member comprises a plurality of interconnected struts that define rows of open cells, and wherein the fixation member is configured to engage cardiac tissue along a non-circumferential portion of a cardiac chamber.

11. The valve repair device of claim 1 wherein the fixation member forms a low-profile frame structure configured to contact a circumferential portion of a cardiac chamber, and wherein the low-profile frame structure includes a connection element affixed to the inner portion of the coaptation member.

12. The valve repair device of claim 1 wherein the coaptation member has a crescent shape along a transverse cross-section of the valve annulus.

13. The valve repair device of claim 1 wherein the coaptation member is configured to extend along a length defined by opposing commissures of the first and second native leaflets.

14. The valve repair device of claim 1 wherein the fixation member comprises a tissue anchor protruding from an inferior portion of the fixation member and configured to penetrate proximate to the native valve annulus.

15. The valve repair device of claim 1 wherein the coaptation member comprises a stent structure configured to be increased in length between opposing commissures of the first and second native leaflets.

16. The valve repair device of claim 1 wherein the coaptation member is configured to adjust in dimension across a cross-sectional length.

17. The valve repair device of claim 16 wherein the coaptation member comprises expandable components to increase in width relative to a commissure line and/or protrusion depth into the native valve orifice.

18. The valve repair device of claim 16 wherein the coaptation member is configured to receive rods that expand the coaptation member in width relative to a commissure line and/or protrusion depth into the native valve orifice.

19. The valve repair device of claim 1 wherein:
   the coaptation member comprises a first locking feature at the inner portion; and
   the plurality of clip mechanisms comprises—
      a first clip mechanism extending from the outer portion of the coaptation member and configured to capture a portion of the second native leaflet; and
      an independent second clip mechanism having a second locking feature configured to engage with the first locking feature to affix the independent second clip mechanism to the inner portion of the coaptation member.

20. The valve repair device of claim 19 wherein the independent second clip mechanism is configured to be housed within the coaptation member before deployment.

21. The valve repair device of claim 19 wherein the first and second locking mechanisms comprise magnetic components.

22. The valve repair device of claim 1 wherein the coaptation surface comprises actuation sections configured to open to capture portions of the first native leaflet.

23. The valve repair device of claim 1, further comprising a leaflet capture component housed in and deployable from the coaptation member and configured to pierce and capture the first native leaflet.

24. The valve repair device of claim 1 wherein each of the clip mechanisms includes a spring-loaded lever configured to move the articulatable arm between an open state and a closed state.

25. The valve repair device of claim 1 wherein the articulatable arm member of one of the clip mechanisms comprises a sub-annular engagement component extending from the free end portion and configured to engage sub-annular cardiac tissue.

26. A valve repair device, comprising:
   a coaptation member configured to be positioned between a posterior leaflet and an anterior leaflet of a mitral valve, the coaptation member comprising—
      a frame structure comprising a plurality of struts;
      a cover extending along at least a portion of the frame structure and configured to form an enclosed chamber within the frame structure, wherein the cover includes an opening to the chamber;
an anterior portion having a surface configured to displace or coapt with the anterior leaflet during systole; and
a posterior portion configured to displace or coapt with at least a portion of the posterior leaflet,
wherein the coaptation member is substantially stationary during cardiac cycles;
a plurality of clip mechanisms depending from the coaptation member, wherein one or more of clip mechanisms comprises—
a base portion coupled to the coaptation member,
an articulatable arm member extending in an upstream direction from the base portion and having a free end portion unaffixed to the coaptation member, wherein the articulatable arm member is configured to capture a portion of the posterior leaflet or the anterior leaflet between the articulatable arm member and coaptation member, and
an actuation mechanism configured to move the articulatable arm member between a closed position and an open position, wherein the actuation mechanism is configured to be actuated via a delivery component inserted through the opening in the cover and into the chamber of the coaptation member.

27. The valve repair device of claim 26 wherein the plurality of clip mechanisms comprises:
a posterior clip mechanism extending from the posterior portion of the coaptation member and configured to capture a portion of the posterior leaflet; and
an anterior clip mechanism extending from the anterior portion of the coaptation member and configured to capture a portion of the anterior leaflet.

28. The valve repair device of claim 26 wherein the plurality of clip mechanisms comprises:
a primary posterior clip mechanism extending from the posterior portion of the coaptation member and configured to capture a central portion of the posterior leaflet; and
a secondary posterior clip mechanism extending from the posterior portion of the coaptation member and configured to capture a lateral portion of the posterior leaflet.

29. The valve repair device of claim 28 wherein the lateral portion is a first lateral portion, and wherein the plurality of clip mechanisms further comprises:
a tertiary clip mechanism extending from the posterior portion of the coaptation member and configured to capture a second lateral portion of the posterior leaflet.

30. The valve repair device of claim 26, further comprising an atrial fixation member coupled to the coaptation member and configured to engage cardiac tissue within a left atrium, wherein the coaptation member extends radially inward from the atrial fixation member.

31. The valve repair device of claim 30 wherein the fixation member comprises a frame structure configured to engage cardiac tissue along a circumferential portion of the left atrium.

32. The valve repair device claim 30 wherein the fixation member comprises a frame structure configured to engage cardiac tissue along a non-circumferential, posterior portion of the left atrium.

33. The valve repair device claim 30 wherein the fixation member comprises a frame structure configured to engage cardiac tissue along a non-circumferential, anterior portion of the left atrium.

34. The valve repair device of claim 30 wherein the coaptation member has a width configured to extend at least across a central scallop of the posterior leaflet.

35. The valve repair device of claim 26 wherein the coaptation member is configured to include an expandable structure for adjusting a width of the coaptation member relative to a commissure line and/or protrusion depth into the native mitral valve orifice.

36. The valve repair device of claim 26 wherein:
the coaptation member comprises a first locking feature at the anterior portion; and
the plurality of clip mechanisms comprises—
a posterior clip mechanism extending from the posterior portion of the coaptation member and configured to capture a portion of the posterior leaflet; and
an independent anterior clip mechanism having a second locking feature configured to engage with the first locking feature to affix the independent second clip mechanism to the inner portion of the coaptation member, wherein the anterior clip mechanism is configured to engage the anterior leaflet.

37. The valve repair device of claim 26 wherein the plurality of clip mechanisms comprises:
a posterior clip mechanism extending from the posterior portion of the coaptation member and configured to capture a portion of the posterior leaflet; and
an independent anterior clip mechanism configured to be housed within the coaptation member and engage the anterior leaflet.

38. The valve repair device of claim 26, further comprising a leaflet capture component housed in and deployable from the coaptation member and configured to pierce and capture the anterior leaflet.

39. The valve repair device of claim 26 wherein each of the clip mechanisms include a spring-loaded lever configured to move the articulatable arm between an open state and a closed state.

40. The valve repair device of claim 26 wherein the articulatable arm member of one of the clip mechanisms comprises a sub-annular engagement component configured to engage sub-annular cardiac tissue.

41. The valve repair device of claim 26 wherein the opening comprises a slit in the cover.

42. The valve repair device of claim 26 wherein the cover extends along at least a superior portion of the frame structure, and wherein the opening is formed in the cover along the superior portion.

43. The valve repair device of claim 26 wherein the delivery component is a flexible tendon.

44. A valve repair device, comprising:
an atrial fixation member configured to press against cardiac tissue proximate to a native valve annulus;
a coaptation member extending away from the atrial fixation member and radially inward from the atrial fixation member, the coaptation member comprising an inner portion having a coaptation surface configured to coapt with a first native leaflet during systole, an outer portion configured to displace at least a portion of a second native leaflet, and a downstream end portion, wherein the coaptation member is substantially stationary during cardiac cycles, and wherein the coaptation defines an interior volume and an opening to the interior volume; and
a plurality of clip mechanisms depending from the coaptation member, wherein each of the clip mechanisms is independently actuatable via a delivery component inserted through the opening in the coaptation member and into the interior volume of the coaptation member to move the clip mechanism between a closed position and an open position.

\* \* \* \* \*